United States Patent
Li et al.

(10) Patent No.: US 12,414,698 B2
(45) Date of Patent: Sep. 16, 2025

(54) DEVICES AND SYSTEMS FOR CONTROLLING PRESSURE DURING SENSING

(71) Applicant: QUALCOMM Incorporated, San Diego, CA (US)

(72) Inventors: Ren Li, San Diego, CA (US); Qilin Lu, San Diego, CA (US); Htet Naing, San Diego, CA (US); Samuel Jon Eubanks, San Diego, CA (US); Kostadin Dimitrov Djordjev, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 69 days.

(21) Appl. No.: 18/478,936

(22) Filed: Sep. 29, 2023

(65) Prior Publication Data
US 2025/0107719 A1   Apr. 3, 2025

(51) Int. Cl.
| | | |
|---|---|---|
| A61B 5/0225 | (2006.01) | |
| A61B 5/00 | (2006.01) | |
| A61B 5/021 | (2006.01) | |
| A61B 5/022 | (2006.01) | |

(52) U.S. Cl.
CPC .......... A61B 5/0225 (2013.01); A61B 5/0095 (2013.01); A61B 5/02125 (2013.01); A61B 5/02225 (2013.01); A61B 5/02233 (2013.01); A61B 5/7264 (2013.01); *A61B 2560/0223* (2013.01)

(58) Field of Classification Search
CPC .............................................. A61B 2560/0223
See application file for complete search history.

(56) References Cited

U.S. PATENT DOCUMENTS

| | | | | |
|---|---|---|---|---|
| 4,349,034 A | * | 9/1982 | Ramsey, III | A61B 5/02141 600/494 |
| 5,255,686 A | * | 10/1993 | Takeda | A61B 5/0225 600/494 |
| 5,474,076 A | * | 12/1995 | Fujita | A61B 5/0225 600/496 |
| 6,440,080 B1 | * | 8/2002 | Booth | A61B 5/022 600/494 |

(Continued)

FOREIGN PATENT DOCUMENTS

WO   2023033983 A1   3/2023

OTHER PUBLICATIONS

International Search Report and Written Opinion—PCT/US2024/048433—ISA/EPO—Dec. 9, 2024.

*Primary Examiner* — Sean D Mattson
(74) *Attorney, Agent, or Firm* — QUALCOMM Incorporated

(57) ABSTRACT

Devices and systems for controlling pressure during sensing are disclosed. Such sensors and/or systems may be embodied in a wearable user device. The wearable user device may include a cuff configured to apply a pressure to a portion of a user at a plurality of discrete pressure levels over a plurality of time periods; a biometric sensor configured to obtain a plurality of sensor measurements associated with a blood vessel of the user at corresponding ones of the plurality of discrete pressure levels during corresponding ones of the plurality of time periods; and a wearable structure including the cuff and the biometric sensor.

26 Claims, 21 Drawing Sheets

(56) References Cited

U.S. PATENT DOCUMENTS

| | | | |
|---|---|---|---|
| 8,840,561 B2* | 9/2014 | Lane | A61B 5/0225 |
| | | | 600/495 |
| 2010/0210956 A1* | 8/2010 | Im | A61B 5/022 |
| | | | 600/490 |
| 2010/0241011 A1 | 9/2010 | McCombie et al. | |
| 2013/0184544 A1* | 7/2013 | Su | A61B 5/0095 |
| | | | 600/407 |
| 2017/0258336 A1* | 9/2017 | Furness, III | A61B 5/026 |
| 2018/0177410 A1* | 6/2018 | Pekander | A61B 5/14551 |
| 2018/0235488 A1* | 8/2018 | Aelen | A61B 5/02225 |
| 2019/0298193 A1* | 10/2019 | Krause | G16H 40/67 |
| 2022/0354375 A1* | 11/2022 | Morimoto | A61B 5/0261 |
| 2023/0034358 A1 | 2/2023 | Elliott et al. | |

\* cited by examiner

DEVICES AND SYSTEMS FOR CONTROLLING PRESSURE DURING SENSING

TECHNICAL FIELD

This disclosure relates generally to devices and systems using biometric sensors.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and/or ambulatory monitoring. Some such devices are, or include, photoacoustic sensors. Although some previously deployed devices can provide acceptable results, improved detection devices and systems would be desirable.

SUMMARY

The systems, methods and devices of this disclosure each have several aspects, no single one of which is solely responsible for the desirable attributes disclosed herein.

In one aspect of the present disclosure, a wearable user device is disclosed. In some embodiments, the wearable user device may include: a cuff configured to apply a pressure to a portion of a user at a plurality of discrete pressure levels over a plurality of time periods; a biometric sensor configured to obtain a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user; and a wearable structure comprising the cuff and the biometric sensor.

In another aspect of the present disclosure, a method of determining a physiological parameter of a user is disclosed. In some embodiments, the method may include: while a pressure is applied to a portion of the user is at a first target pressure level at a first time, obtaining one or more first sensor measurements from a blood vessel of the user, the one or more first sensor measurements correlating to first data of a characteristic of the blood vessel; while the pressure applied to the portion of the user is at a second target pressure level at a second time, obtaining one or more second sensor measurements from the blood vessel of the user, the one or more second sensor measurements correlating to second data of the characteristic of the blood vessel; and determining the physiological parameter of the user based at least on the first data and the second data of the characteristic of the blood vessel.

In another aspect of the present disclosure, an apparatus is disclosed. In some embodiments, the apparatus may include: means for applying a pressure to a portion of a user at a plurality of discrete pressure levels over a plurality of time periods; means for obtaining a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user; and wearable means comprising the means for applying the pressure to the portion of the user, and the means for obtaining the plurality of sensor measurements.

In another aspect of the present disclosure, a non-transitory computer-readable apparatus is disclosed. In some embodiments, the non-transitory computer-readable apparatus may include a storage medium, the storage medium including a plurality of instructions configured to, when executed by one or more processors, cause an apparatus to: while a pressure is applied to a portion of the user is at a first target pressure level at a first time, obtain one or more first sensor measurements from a blood vessel of the user, the one or more first sensor measurements correlating to first data of a characteristic of the blood vessel; while the pressure applied to the portion of the user is at a second target pressure level at a second time, obtain one or more second sensor measurements from the blood vessel of the user, the one or more second sensor measurements correlating to second data of the characteristic of the blood vessel; and determine the physiological parameter of the user based at least on the first data and the second data of the characteristic of the blood vessel.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1:
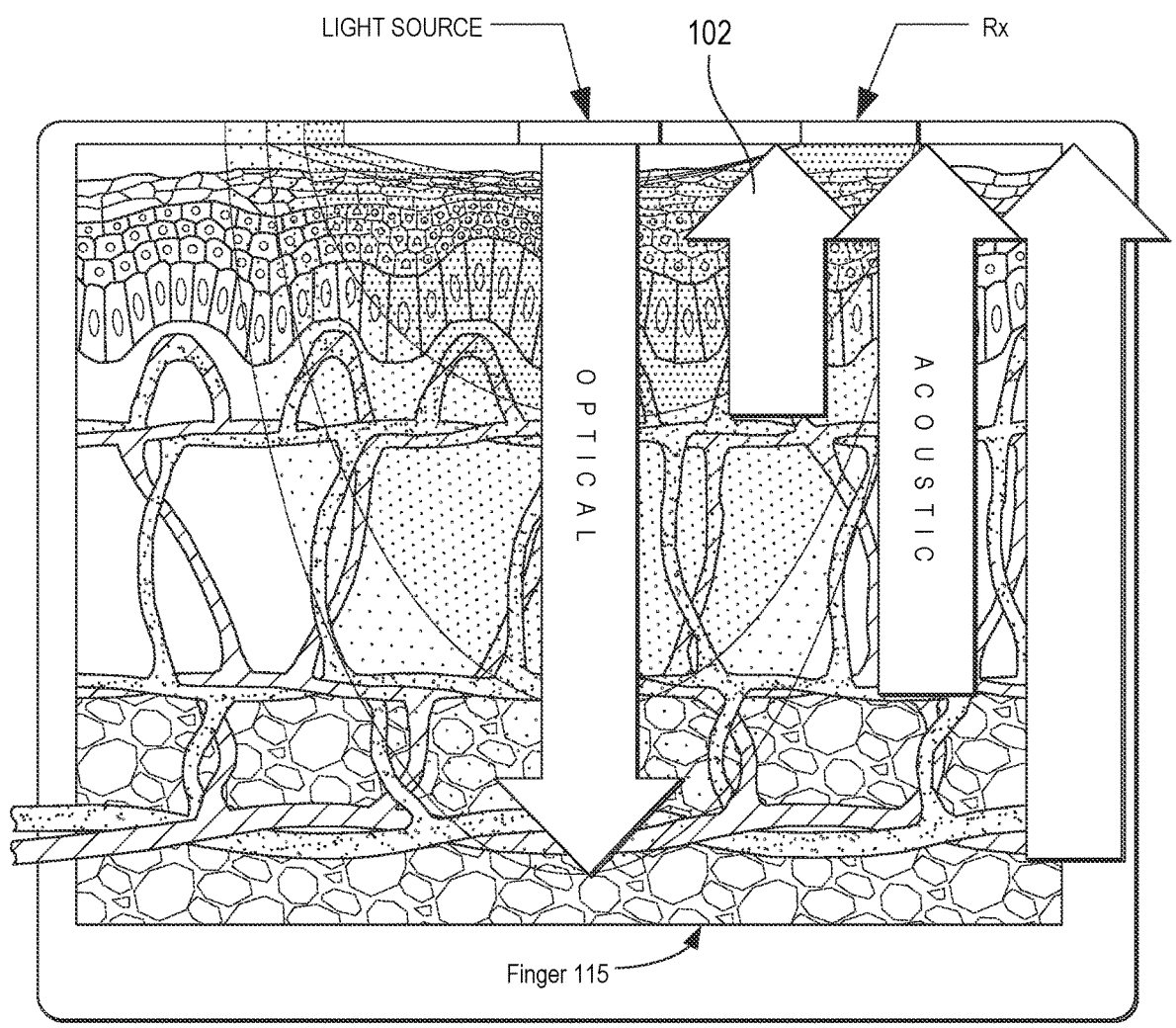
FIG. 1 shows an example of a blood pressure monitoring device based on photoacoustic plethysmography, which may be referred to herein as PAPG.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications or monitoring of other physiological parameters. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, chest bands, anklets, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

There is a strong need for accurate, non-invasive, continuous monitoring wearable devices for both clinical and consumer applications, e.g., for measuring physiological parameters such as blood pressure of a user. In particular, non-invasive monitoring of blood pressure is desirable. Continuous blood pressure monitoring opens avenues for efficient and effective diagnosis and treatment of cardiovascular conditions (e.g., hypertension), cardiovascular event detection, and stress monitoring. It would also allow daily spot checks of cardiovascular conditions including blood pressure, as well as overnight sleep monitoring. Positive user experience during overnight sleep monitoring is desirable. For example, there should be minimal discomfort to the user during operation of the wearable device, including during sleep.

Sensing mechanisms that allow efficient collection of biometric measurements (photoacoustic measurements, optical measurements, etc.) and measurements of physiological characteristics such as pulse wave velocity (PWV) of a blood vessel, blood pressure of the user, could be a step in that direction. Existing cuff-based blood pressure measurement methods such as oscillometry and artery volume clamp require the usage of a counter-pressure cuff and pressure control. Pulse wave analysis (PWA) using an oscillometer can determine blood pressure by inflating a cuff worn by a user to a high pressure to cut off blood flow, and releasing the cuff pressure gradually while measuring the pulse wave with a pressure sensor. A waveform representing arterial blood pressure is analyzed to estimate the blood pressure non-invasively. Regular calibration may be required. Artery volume clamp involves arteries in a finger clamped at a constant diameter by applying external cuff pressure to the finger. The clamp system may have a built-in optical (PPG) sensor, a fast pneumatic servo system (a pulsating cuff pressure is applied to the finger arteries that are precisely opposite to the intra-arterial pressure), and a dynamic servo setpoint adjuster (for automated calibration to keep track of the correct setpoint level of the finger blood pressure). When the cuff pressure equals the arterial pressure, the transmural pressure inside relative to outside is zero. Another traditional method is tonometry, which measures arterial pressure by applying force (e.g., using a cuff) over a superficial artery (e.g., radial artery) to distort the vessel, and a probe measures arterial displacement due to arterial pulsation are regarded to be proportional to the intra-arterial pressure. This method is prone to error and requires cuff calibration.

Photoacoustic measurements provide valuable data for determining characteristics of a blood vessel. For example, arterial dimensions can be determined based on photoacoustic measurements, and pulse wave velocity (PWV) of a blood vessel can be determined using the arterial dimensions. PWV is a function of the arterial wall stiffness and tension, blood density, body posture, blood pressure, etc. Hence, PWV is a relevant characteristic of interest, since biometrics and physiological parameters of a person (such as blood pressure) are correlated with PWV. Accurate and flexible PWV measurements that can be obtained conveniently and efficiently (e.g., with a single device or system), along with other information such as artery diameter and distention, are valuable for continuous and non-invasive tracking of biometrics and physiological parameters. It would thus be valuable for blood pressure estimation to obtain such information with accuracy and convenience, including as a wearable device.

Wearable devices configured to apply pressure using a cuff system require a small form factor pump that can run quietly and power efficiently. For this reason, a piezoelectric transducer pump can be used, as it has a simple structure, requires low power, and can operate at the ultrasound frequency range, inaudible to the human ear. Advantageously, using pressure feedback from the cuff system (ideally proximate the location of a photoacoustic sensor) can control the target pressure precisely and automatically to enhance user experience (e.g., support overnight sleep monitoring, including remotely) without the need for pressure calibration.

However, various issues can arise when operating the device with the pump. One issue is noise. A bladder or airbag will inflate and deflate to apply the pressure. The airbag will be inflated by air when power is applied to the pump, and deflate when power is removed from the pump. In some cases, the pump may not be designed to maintain pressure at the constant (or substantially constant) pressure value needed for accurate photoacoustic measurements and PWV measurements. The target pressure may drop when power to the pump is off, so maintaining the pressure may require intermittent or frequent inflation. Inflation and deflation cause noise. Moreover, even though the pump can operate at the ultrasound frequency range, it may still cause audible noise as a result of the nonlinear ultrasound effect (propagation of ultrasonic waves is nonlinear) or mechanical noises through structure coupling. The device may include and operate other sensors such as photoacoustic sensors, microphones, etc. which are sensitive to sound and noise. Hence, it is desirable to avoid or mitigate noise caused during pump operation while obtaining photoacoustic (or other acoustic, e.g., microphone) sensor measurements while maintaining a target pressure in the airbag.

Another issue is that pressure is sensitive to temperature and altitude. For example, the temperature of the air inside the airbag can rise 10 degrees Celsius for every 30 seconds of continuous pump operation. As noted above, a substantially constant pressure level may be needed for accurate photoacoustic measurements and PWV measurements. This natural rise in temperature from operating the pump can change the pressure and adversely affect measurements.

Although applying pulse-width modulation (PWM) voltage to the pump can hold the airbag pressure to a target value, audible sounds can be heard from passive valve movement (e.g., of a check valve). The sound frequency depends on the PWM frequency. The pressure could also show ripple effects from the constant inflation (power on) or deflation (power off).

Adding to the issues is that a piezoelectric transducer pump is difficult to control precisely because of intrinsic behaviors of piezoelectric material like non-linearity and hysteresis. Air pressure created by a pump driver via a voltage calibrated based on a particular temperature and altitude can result in overshooting or undershooting the target pressure. The actual target pressure can also change because of temperature variation and altitude changes.

To address the various issues above, embodiments of sensor apparatus disclosed herein provide various mechanisms for obtaining accurate sensor measurements while avoiding noise and pressure variations. In some embodiments, discrete pressure levels may be externally applied by a bladder or airbag of a cuff to a user using or wearing the cuff. Precise and discrete pressure levels can be applied based on a voltage level applied to a pump, which causes the bladder to inflate while a vent is closed. To deflate, the vent may be opened below a target pressure level and/or the pump may increase the pressure to the target level. Each discrete pressure level can each be held for a period of time while sensor measurements are being taken. Photoacoustic sensors in particular may experience little to no noise during this time because the pressure is held to a target pressure level by a closed vent and there is no mechanical or acoustic interference from pump operation, air flow, deflation, etc.

In addition, embodiments disclosed herein can use a feedback loop to keep the pressure level at a target pressure level. If the current pressure is lower or higher than the intended target pressure level (whether caused by temperature or altitude variation, prolonged operation of the sensor apparatus, or any other reason), feedback information (e.g., pressure, voltage) from a pressure sensor of the sensor apparatus can be compared with target information (e.g., pressure, voltage). Depending on the implementation, fuzzy logic, a neural network, and/or a PID (proportional-integral-derivative) controller can be used to determine whether to correct the deviated pressure and determine the appropriate voltage for the pump or control signal for the vent.

Finally, photoacoustic measurements (and thus PWVs) at corresponding pressure levels provide data that can be used to estimate a physiological parameter of the user (e.g., blood pressure). In some implementations, a predictive machine learning or artificial intelligence model can be trained to predict the blood pressure. In some implementations, the predictive model can be trained to output a control signal (e.g., indicative of voltage to be applied to correct the pressure level). In addition, based on any discrepancies between the sensor-based estimation and the model-generated prediction, some or all of the sensor-based measurements can be kept or discarded.

Particular implementations of the subject matter described in this disclosure can be implemented to realize one or more of the following potential advantages. Making photoacoustic, acoustic (e.g., microphone), or other noise-sensitive biometric measurements at discrete pressure levels while sources of noise are not operational can result in clean information that is not prone to error, outliers, etc. The approaches described herein can result in information that is useful for estimating parameters such as blood pressure, contributing to higher accuracy of a monitoring device that is also non-invasive and capable of continuous measurements (including during sleep). The data collected is also compatible with machine learning or deep learning implementations, where the data can be used as input to a machine learning or artificial intelligence model and further improve the accuracy of the blood pressure.

Additional details will follow after an initial description of relevant systems and technologies.

FIG. 1 shows an example of a blood pressure monitoring device based on photoacoustic plethysmography, which is referred to herein as PAPG. FIG. 1 shows the same examples of arteries, veins, arterioles, venules and capillaries inside a body part, which is a finger 115 in this example. In some examples, the light source shown in FIG. 1 may be coupled to a light source system (not shown) that is disposed remotely from the body part (e.g., finger 115). In some implementations, the light source may be an opening of an optical fiber or other waveguide. Such an opening may also be connected to an opening of an interface that is contactable with the body part. In some embodiments, the light source system may include one or more LEDs, one or more laser diodes, etc. In this example, the light source has transmitted light (in some examples, green, red, infrared, and/or near-infrared (NIR) light) that has penetrated the tissues of the finger 115 in an illuminated zone.

In the example shown in FIG. 1, blood vessels (and components of the blood itself) are heated by the incident light from the light source and are emitting acoustic waves 102. In this example, the emitted acoustic waves 102 include ultrasonic waves. According to this implementation, the acoustic wave emissions 102 are being detected by an acoustic receiver. In some embodiments, the acoustic receiver may be an ultrasonic receiver, which is a piezoelectric receiver in this example. Photoacoustic emissions 102 from the illuminated tissues, detected by the acoustic receiver, may be used to detect volumetric changes in the blood of the illuminated zone of the finger 115 that correspond to physiological data within the illuminated tissues of finger 115, such as heart rate waveforms. Although some of the tissue areas shown to be illuminated are offset from those shown to be producing photoacoustic emissions 102, this is merely for illustrative convenience. It will be appreciated that that the illuminated tissues will actually be those producing photoacoustic emissions. Moreover, it will be appreciated that the maximum levels of photoacoustic emissions will often be produced along the same axis as the maximum levels of illumination.

One important difference between an optical technique such as a photoplethysmography (PPG)-based system the PAPG-based method of FIG. 1 is that the acoustic waves shown in FIG. 1 travel much more slowly than the reflected light waves involved in PPG. Accordingly, depth discrimination based on the arrival times of the acoustic waves shown in FIG. 1 is possible, whereas depth discrimination based on the arrival times of the light waves in PPG may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 2:
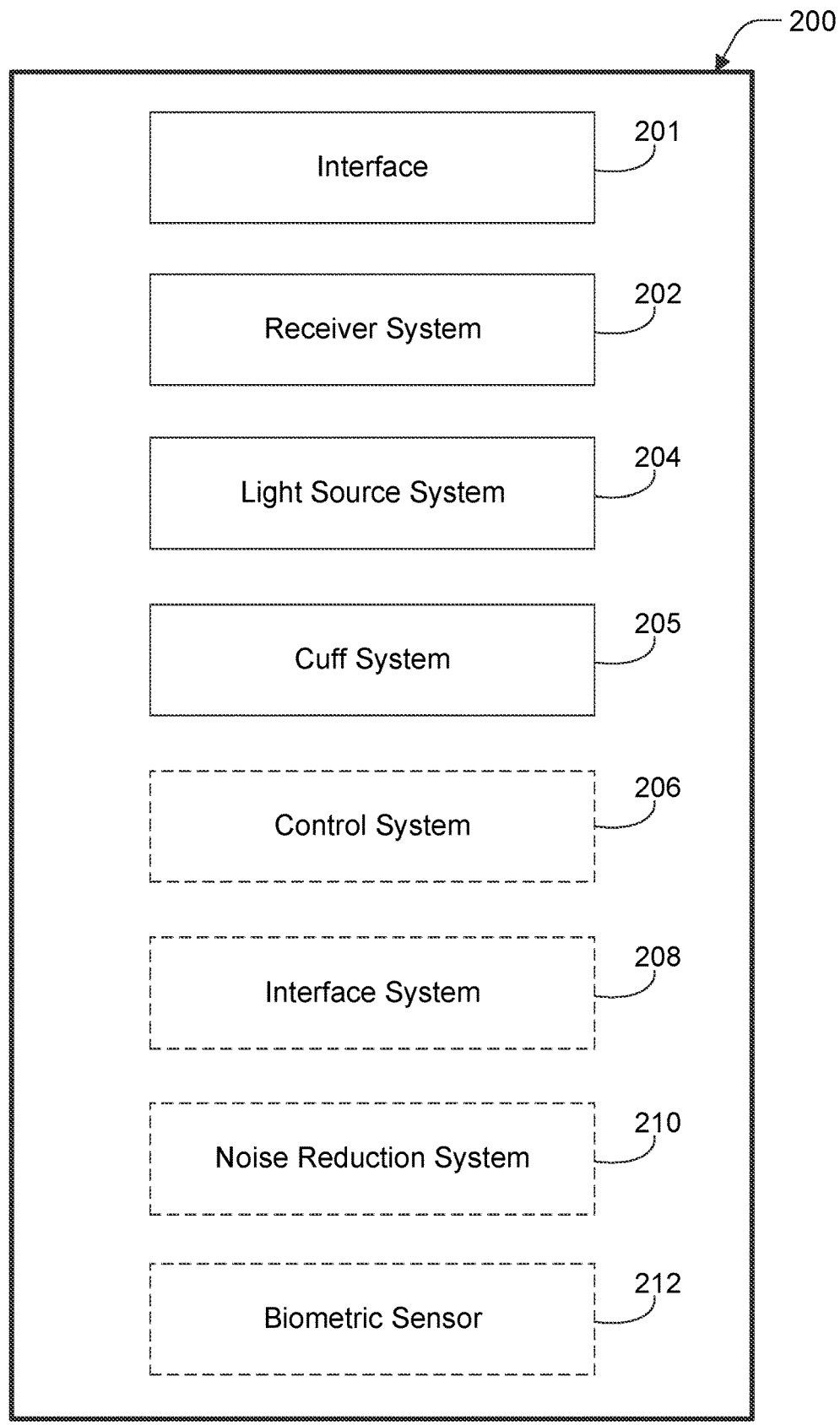
FIG. 2 is a block diagram that shows example components of a sensor apparatus according to some disclosed implementations.

FIG. 2 is a block diagram that shows example components of a sensor apparatus 200 according to some implementations. In this example, the sensor apparatus 200 includes an interface 201, a receiver system 202, a light source system 204, and a cuff system 205. In some cases, a waveguide system may be included as a separate part of the sensor apparatus 200, or in some cases, may be part of the light source system 204. Some implementations of the sensor apparatus 200 may include a control system 206, an interface system 208, a noise reduction system 210, a biometric sensor 212, or a combination thereof.

Various examples of the interface 201 and various configurations of the receiver system 202 and the light source system 204 are disclosed herein. Some examples are described in more detail below.

In some embodiments, the interface 201, the receiver system 202, and the light source system 204 may be components of a photoacoustic (PAPG) sensor of the sensor apparatus 200. That is to say, in some embodiments, the sensor apparatus 200 may include a photoacoustic sensor and a cuff system 205. In various implementations described herein, the photoacoustic sensor and/or its components may operate in concert with the cuff system 205, e.g., timing the acquisition of photoacoustic measurements in relation to the operation of the cuff system 205, which will be described in greater detail following the example configurations of the example components of a sensor apparatus 200.

Some disclosed PAPG sensors described herein may include a platen, a light source system, and an ultrasonic receiver system. According to some implementations, the light source system may include a light source configured to produce and direct light. In some implementations, the platen may include an anti-reflective layer, a mirror layer, or combinations thereof. According to some implementations, the platen may have an outer surface, or a layer on the outer surface, with an acoustic impedance that is configured to approximate the acoustic impedance of human skin. In some implementations, the platen may have a surface proximate the ultrasonic receiver system, or a layer on the surface proximate the ultrasonic receiver system, with an acoustic impedance that is configured to approximate the acoustic impedance of the ultrasonic receiver system.

Some disclosed PAPG sensors described herein may include an interface, a light source system and an ultrasonic receiver system. Some such devices may not include a rigid platen. According to some implementations, the interface may be a physical, flexible interface constructed of one or more of suitable materials having a desired property or properties (e.g., an acoustic property such as acoustic impedance, softness of the material). In some implementations, the interface may be a flexible interface that can contact a target object that may be proximate to or contact the interface. There may be salient differences between such an interface and a platen. In some implementations, the light source system may be configured to direct light using one or more optical waveguides (e.g., optical fibers) configured to direct light toward a target object. According to some implementations, the interface may have an outer surface, or a layer on the outer surface, with an acoustic impedance that is configured to approximate the acoustic impedance of human skin. Such outer surface may have a contact portion that is contactable by a user or a body part of the user (e.g., finger, wrist). In some examples, the optical waveguide(s) may be embedded in one or more acoustic matching layers that are configured to bring the light transmitted by the optical waveguide(s) very close to tissue. The outer surface and/or other parts of the interface may be compliant, pliable, flexible, or otherwise at least partially conforming to the shape and contours of the body part of the user. In some implementations, the interface may have a surface proximate the ultrasonic receiver system, or a layer on the surface proximate the ultrasonic receiver system, with an acoustic impedance that is configured to approximate the acoustic impedance of the ultrasonic receiver system.

In some implementations in which the receiver system 202 includes an ultrasonic receiver system, the interface 201 may be an interface having a contact portion configured to make contact with a body part of a user such as the finger 115 shown in FIG. 1.

In some embodiments, the light source system 204 may, include one or more one or more light sources. In some implementations, the light source system 204 may include one or more light-emitting diodes. In some implementations, the light source system 204 may include one or more laser diodes. According to some implementations, the light source system 204 may include one or more vertical-cavity surface-emitting lasers (VCSELs). In some implementations, the light source system 204 may include one or more edge-emitting lasers. In some implementations, the light source system 204 may include one or more neodymium-doped yttrium aluminum garnet (Nd:YAG) lasers.

Hence, the light source system 204 may include, for example, a laser diode, a light-emitting diode (LED), or an array of either or both. The light source system 204 may be configured to generate and emit optical signals. The light source system 204 may, in some examples, be configured to transmit light in one or more wavelength ranges. In some examples, the light source system 204 may be configured to transmit light in a wavelength range of 500 to 600 nanometers (nm). According to some examples, the light source system 204 may be configured to transmit light in a wavelength range of 800 to 950 nm. According to some examples, the light source system 204 may be configured to transmit light in infrared or near infrared (NIR) region of the electromagnetic spectrum (about 700 to 2500 nm). In view of factors such as skin reflectance, fluence, the absorption coefficients of blood and various tissues, and skin safety limits, one or both of these wavelength ranges may be suitable for various use cases. For example, the wavelength ranges of 500 nm to 600 nm and of 800 to 950 nm may both be suitable for obtaining photoacoustic responses from relatively smaller, shallower blood vessels, such as blood vessels having diameters of approximately 0.5 mm and depths in the range of 0.5 mm to 1.5 mm, such as may be found in a finger. The wavelength range of 800 to 950 nm, or about 700 to 900 nm, or about 600 to 1100 nm may, for example, be suitable for obtaining photoacoustic responses from relatively larger, deeper blood vessels, such as blood vessels having diameters of approximately 2.0 mm and depths in the range of 2 mm to 3 mm, such as may be found in an adult wrist. In some implementations, the light source system 204 may be configured to switch wavelengths to capture acoustic information from different depths, e.g., based on signal(s) from the control system 206.

In some implementations, the light source system 204 may be configured for emitting various wavelengths of light, which may be selectable to trigger acoustic wave emissions primarily from a particular type of material. For example, because the hemoglobin in blood absorbs near-infrared light very strongly, in some implementations the light source system 204 may be configured for emitting one or more wavelengths of light in the near-infrared range, in order to trigger acoustic wave emissions from hemoglobin. However, in some examples, the control system 206 may control the wavelength(s) of light emitted by the light source system 204 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the receiver system 202. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying range gate delays (RGDs)) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 204 may be configured for emitting a light pulse with a pulse width less than about 100 nanoseconds. In some implementations, the light pulse may have a pulse width between about 10 nanoseconds and about 500 nanoseconds or more. According to some examples, the light source system 204 may be configured for emitting a plurality of light pulses at a pulse repetition frequency between 10 Hz and 100 kHz. Alternatively, or additionally, in some implementations the light source system 204 may be configured for emitting a plurality of light pulses at a pulse repetition frequency between about 1 MHz and about 100 MHz. Alternatively, or additionally, in some implementations the light source system 204 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 204 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 204. In some implementations, the light source system 204 may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

According to some examples, the light source system 204 may also include one or more light-directing elements configured to direct light from the light source system 204 towards the target object along the first axis. In some examples, the one or more light-directing elements may include at least one diffraction grating. Alternatively, or additionally, the one or more light-directing elements may include at least one lens.

In various configurations, the light source system 204 may incorporate anti-reflection (AR) coating, a mirror, a light-blocking layer, a shield to minimize crosstalk, etc.

The light source system 204 may include various types of drive circuitry, depending on the particular implementation. In some disclosed implementations, the light source system 204 may include at least one multi-junction laser diode, which may produce less noise than single-junction laser diodes. In some examples, the light source system 204 may include a drive circuit (also referred to herein as drive circuitry) configured to cause the light source system 204 to emit pulses of light at pulse widths in a range from 3 nanoseconds to 1000 nanoseconds. According to some examples, the light source system 204 may include a drive circuit configured to cause the light source system 204 to emit pulses of light at pulse repetition frequencies in a range from 1 kilohertz to 100 kilohertz.

In some example implementations, some or all of the one or more light sources of the light source system 204 may be disposed at or along an axis that is parallel to or angled relative to a central axis associated with the platen or interface 201. Optical signals may be emitted toward a target object (e.g., blood vessel), which may cause generation of ultrasonic waves by the target object. These ultrasonic waves may be detectable by one or more receiver elements of a receiver system 202.

Various examples of a receiver system 202 are disclosed herein, some of which may include acoustic receiver systems (e.g., ultrasonic receiver systems), optical receiver systems, or combinations thereof. In some implementations, the receiver system 202 includes an ultrasonic receiver system having the one or more receiver elements. In implementations that include an ultrasonic receiver system, the ultrasonic receiver and an ultrasonic transmitter may be combined in an ultrasonic transceiver. In some examples, the receiver system 202 may include a piezoelectric receiver layer, such as a layer of PVDF polymer or a layer of PVDF-TrFE copolymer. In some implementations, a single piezoelectric layer may serve as an ultrasonic receiver. In some implementations, other piezoelectric materials may be used in the piezoelectric layer, such as aluminum nitride (AlN) or lead zirconate titanate (PZT). The receiver system 202 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the receiver system 202 may be, or may include, an ultrasonic receiver array. In some examples, the sensor apparatus 200 may include one or more separate ultrasonic transmitter elements or one or more separate arrays of ultrasonic transmitter elements. In some examples, the ultrasonic transmitter(s) may include an ultrasonic plane-wave generator.

In some implementations, at least portions of the sensor apparatus 200 (for example, the receiver system 202, the light source system 204, or both) may include one or more sound-absorbing layers, acoustic isolation material, light-absorbing material, light-reflecting material, or combinations thereof. In some examples, acoustic isolation material may reside between the light source system 204 and at least a portion of the receiver system 202. In some examples, at least portions of the sensor apparatus 200 (for example, the receiver system 202, the light source system 204, or both) may include one or more electromagnetically shielded transmission wires. In some such examples, the one or more electromagnetically shielded transmission wires may be configured to reduce electromagnetic interference from the light source system 204 that is received by the receiver system 202.

In some embodiments, the sensor apparatus 200 may include a cuff system 205. The cuff system 205 may include, in some implementations, a pump, a bladder, and/or a pressure sensor. Further components of the cuff system 205 may include a vent, a pump driver, a controller, a printed circuit board, a temperature sensor, a memory, a processor, a valve, a nozzle, a tube, a power source or battery, a physical structure (e.g., a wearable structure, a housing, a cuff), or some combination thereof.

The pump may be configured to flow air into the bladder to cause positive pressure within the bladder. The bladder may be an air bag constructed to be pressurized by the air contained therein. In some configurations, a pump driver (including, e.g., circuitry, logic, processor) may control the pump and cause the influx of air into the bladder. Voltage may be applied to the pump by the pump driver or the controller to control the influx of air. In some implementations, the pressure caused by the air may be constant over a period of time. Such pressure may be changed incrementally by adjusting a voltage level. Hence, external pressure may be applied and held at discrete pressure levels. A vent may also be controlled by the controller to allow air to escape the bladder, which reduces the pressure. The pressure sensor may be used to detect the pressure inside the bladder, resulting in pressure data for operations described herein. The pressure can be adjusted to a prescribed level based on the detected pressure. Components of the cuff system 205 will be discussed in further detail below in relation to system embodiments.

The control system 206 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 206 also may include (and/or be configured for communication with) one or more memory devices, such as one or more random access memory (RAM) devices, read-only memory (ROM) devices, etc. Accordingly, the sensor apparatus 200 may have a memory system that includes one or more memory devices, though the memory system is not shown in FIG. 2. The control system 206 may be configured for receiving and processing data from the receiver system 202, e.g., as described below. If the sensor apparatus 200 includes an ultrasonic transmitter, the control system 206 may be configured for controlling the ultrasonic transmitter. In some implementations, functionality of the control system 206 may be partitioned between one or more controllers or processors, such as a dedicated sensor controller and an applications processor of a mobile device.

In some examples, the control system 206 may be communicatively coupled to the light source system 204 and configured to control the light source system to emit light towards a target object on an outer surface of the interface 201. In some such examples, the control system 206 may be configured to receive signals from the ultrasonic receiver system (including one or more receiver elements) corresponding to the ultrasonic waves generated by the target object responsive to the light from the light source system. In some examples, the control system 206 may be configured to identify one or more blood vessel signals, such as arterial signals or vein signals, from the ultrasonic receiver system. In some such examples, the one or more arterial signals or vein signals may be, or may include, one or more blood vessel wall signals corresponding to ultrasonic waves generated by one or more arterial walls or vein walls of the target object. In some such examples, the one or more arterial signals or vein signals may be, or may include, one or more arterial blood signals corresponding to ultrasonic waves generated by blood within an artery of the target object or one or more vein blood signals corresponding to ultrasonic waves generated by blood within a vein of the target object. In some examples, the control system 206 may be configured to determine or estimate one or more physiological parameters or cardiac features based, at least in part, on one or more arterial signals, on one or more vein signals, or on combinations thereof. According to some examples, a physiological parameter may be, or may include, blood pressure. In some approaches, blood pressure can be estimated based at least on PWV, as will be discussed below.

In further examples, the control system 206 may be communicatively coupled to the receiver system 202. The receiver system 202 may be configured to detect acoustic signals from the target object. The control system 206 may be configured to select at least one of a plurality of receiver elements of the receiver system 202. Such selected receiver element(s) may correspond to the best signals from multiple receiver elements. In some embodiments, the selection of the at least one receiver element may be based on information regarding detected acoustic signals (e.g., arterial signals or vein signals) from the plurality of receivers. For example, signal quality or signal strength (based, e.g., on signal-to-noise ratio (SNR)) of some signals may be relatively higher than some others or above a prescribed threshold or percentile, which may indicate the best signals. In some implementations, the control system 206 may also be configured to, based on the information regarding detected acoustic signals, determine or estimate at least one characteristic of the blood vessels such as PWV (indicative of arterial stiffness), arterial dimensions, or both.

Some implementations of the sensor apparatus 200 may include an interface system 208. In some examples, the interface system 208 may include a wireless interface system. In some implementations, the interface system 208 may include a user interface system, one or more network interfaces, one or more interfaces between the control system 206 and a memory system and/or one or more interfaces between the control system 206 and one or more external device interfaces (e.g., ports or applications processors), or combinations thereof. According to some examples in which the interface system 208 is present and includes a user interface system, the user interface system may include a microphone system, a loudspeaker system, a haptic feedback system, a voice command system, one or more displays, or combinations thereof. According to some examples, the interface system 208 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 208 may include a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some implementations, the force sensor system may be mechanically coupled to a platen. In some such examples, the force sensor system may be integrated into circuitry of the ultrasonic fingerprint sensor. In some examples, the interface system 208 may include an optical sensor system, one or more cameras, or a combination thereof.

According to some examples, the sensor apparatus 200 may include a noise reduction system 210. For example, the noise reduction system 210 may include one or more mirrors that are configured to reflect light from the light source system 204 away from the receiver system 202. In some implementations, the noise reduction system 210 may include one or more sound-absorbing layers, acoustic isolation material, light-absorbing material, light-reflecting material, or combinations thereof. In some examples, the noise reduction system 210 may include acoustic isolation material, which may reside between the light source system 204 and at least a portion of the receiver system 202, on at least a portion of the receiver system 202, or combinations thereof. In some examples, the noise reduction system 210 may include one or more electromagnetically shielded transmission wires. In some such examples, the one or more electromagnetically shielded transmission wires may be configured to reduce electromagnetic interference from circuitry of the light source system, receiver system circuitry, or combinations thereof, that is received by the receiver system.

In some embodiments, the sensor apparatus 200 may be a wearable device configured to be worn by a user, e.g., around the wrist, finger, arm, leg, ankle, or another appendage, or another portion of the body. In an example implementation, the sensor apparatus 200 may have the form of a wristwatch and can be worn around the wrist. The cuff system 205 may apply pressure around the wrist, while the skin at the wrist makes contact via the interface 201 and photoacoustic measurements can be taken by virtue of operating the receiver system 202 and the light source system 204. However, the embodiments described herein are not so limited. In certain cases, the components of the sensor apparatus 200 may not all be worn. For instance, the cuff system 205 may be worn around an appendage, similar to a sphygmomanometer, but other components such as the receiver system 202 and the light source system 204 may be in a separate PAPG sensor component and/or not be in a wearable chassis in order to collect photoacoustic measurements.

In some implementations, the photoacoustic sensor and/or its components may operate in concert with at least one biometric sensor 212. One example of the biometric sensor 212 may be an optical sensor, such as a photoplethysmography (PPG) sensor configured to operate according to principles described with respect to FIG. 3 below. In addition or alternatively, biometric sensor 212 may include an ultrasound sensor (e.g., ultrasound transmitter and ultrasound receiver) or other acoustic sensor (e.g., microphone), speckleplethysmography (SPG) sensor, and/or an electrocardiogram (EKG) electrode or sensor. In fact, any desired type of biometric sensor may be used. It many implementations, the biometric sensor may have contact with skin (which may occur via the interface 201) to acquire consistent and useful sensor data. Strictly speaking, the photoacoustic sensor (including the interface 201, the receiver system 202, and the light source system 204) may also be referred to as a biometric sensor. However, the biometric sensor 212 may optionally provide an additional sensing modality, such as PPG. Such biometric sensor 212 may or may not necessarily be used in conjunction with the cuff system 205.

Figure 3:
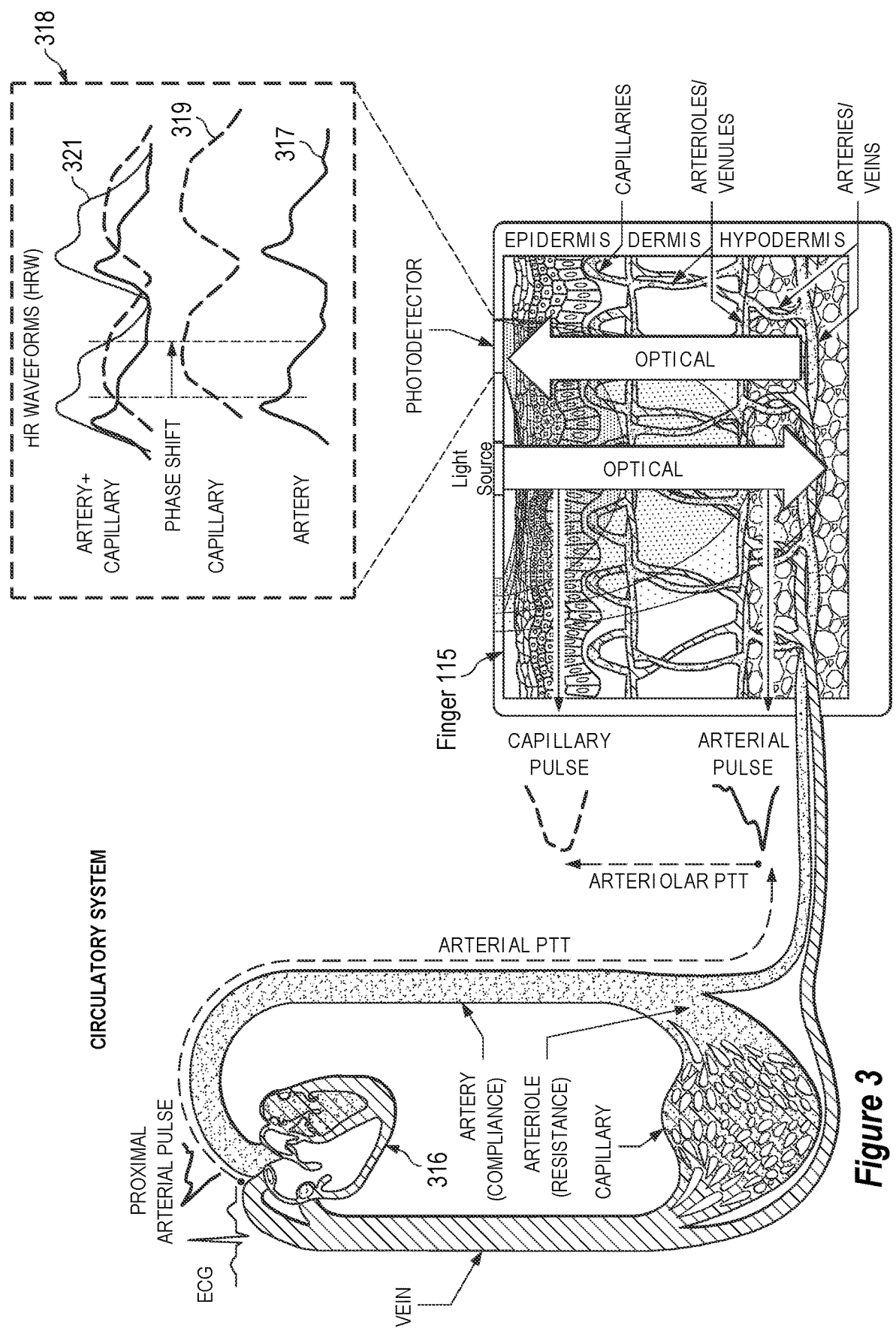
FIG. 3 shows an example of a blood pressure monitoring device based on photoplethysmography (PPG).

FIG. 3 shows an example of a blood pressure monitoring device based on photoplethysmography (PPG). FIG. 3 shows examples of arteries, veins, arterioles, venules and capillaries of a circulatory system, including those inside a finger 115. In the example shown in FIG. 3, an electrocardiogram (EKG) sensor has detected a proximal arterial pulse near the heart 316. Some examples are described below of measurement of the arterial pulse transit time (PTT) according to arterial pulses measured by two sensors, one of which may be an electrocardiogram sensor in some implementations.

According to the example shown in FIG. 3, a light source that includes one or more lasers or light-emitting diodes (LEDs) has transmitted light (in some examples, green, red, infrared, and/or near-infrared (NIR) light) that has penetrated the tissues of the finger 115 in an illuminated zone. Reflections from these tissues, detected by a photodetector, may be used to detect volumetric changes in the blood of the illuminated zone of the finger 115 that correspond to heart rate waveforms.

As shown in the heart rate waveform graphs 318 of FIG. 3, the capillary heart rate waveform 319 is differently-shaped and phase-shifted relative to the artery heart rate waveform 317. In this simple example, the detected heart rate waveform 321 is a combination of the capillary heart rate waveform 319 and the artery heart rate waveform 317. In some instances, the responses of one or more other blood vessels may also be part of the heart rate waveform 321 detected by a PPG-based blood pressure monitoring device.

Figure 4:
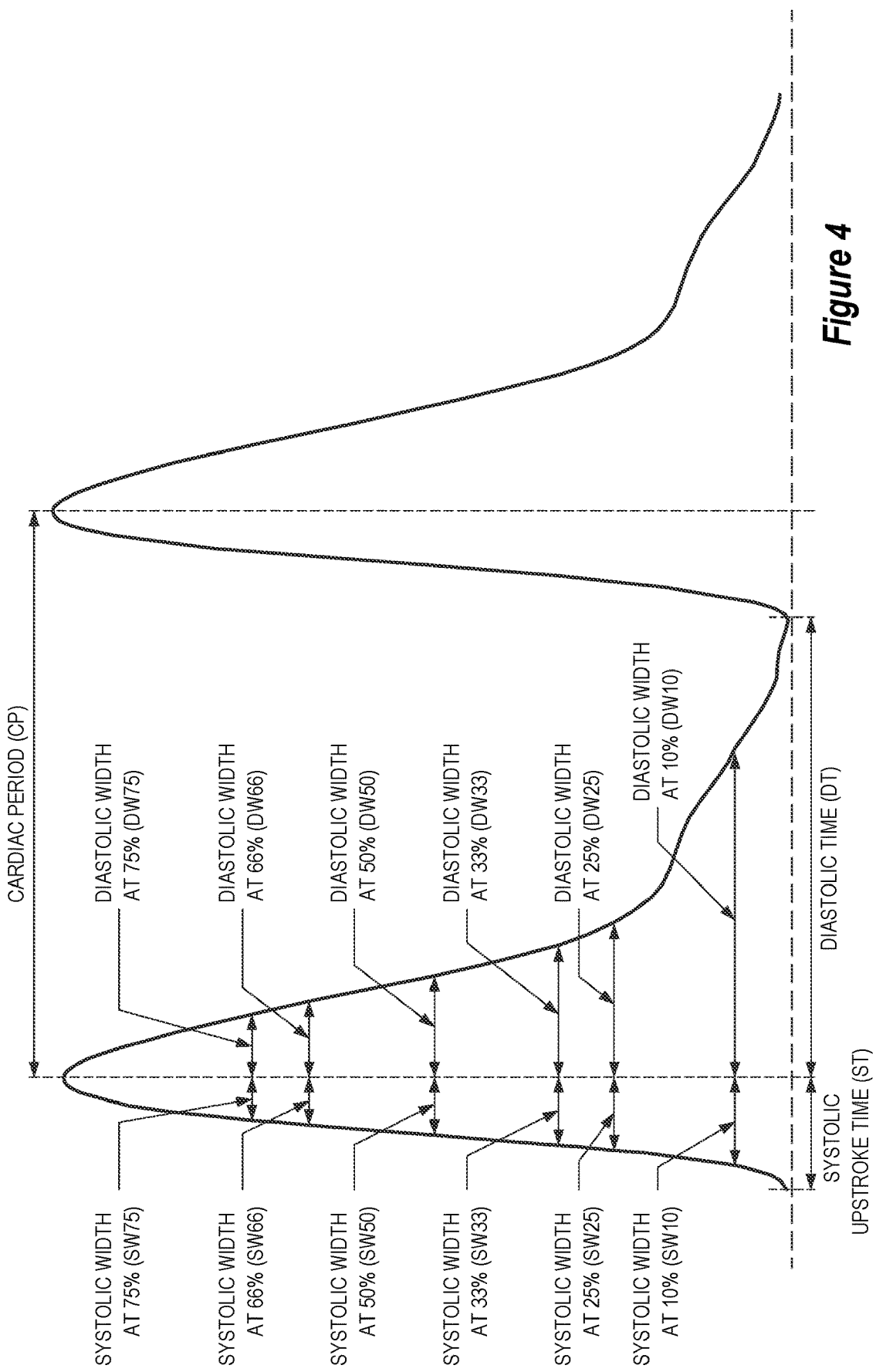
FIG. 4 shows examples of heart rate waveform (HRW) features that may be extracted according to some implementations.

FIG. 4 shows examples of heart rate waveform (HRW) features that may be extracted according to some implementations. The horizontal axis of FIG. 4 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 4 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50)/(DW10+SW10), etc.

Figure 5A:
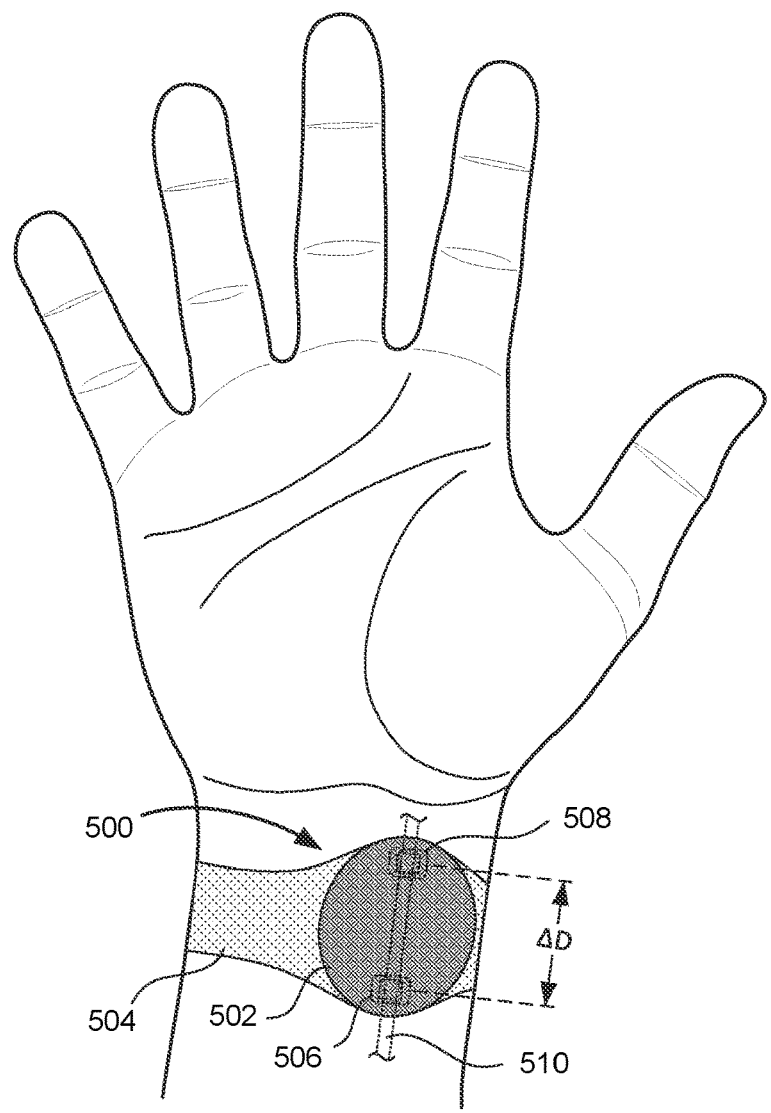
FIG. 5A shows an example monitoring device designed to be worn around a wrist according to some implementations.

In some implementations, the monitoring device can be positioned around a wrist of a user with a strap or band, similar to a watch or fitness/activity tracker. FIG. 5A shows an example device 500 designed to be worn around a wrist according to some implementations. In some embodiments, the example device 500 may include the sensor apparatus 200 so as to allow components of the sensor apparatus 200 to interact with the user, e.g., via the skin of the user. In the illustrated example, the monitoring device 500 includes a housing 502 integrally formed with, coupled with or otherwise integrated with a wristband 504. The first and the second arterial sensors 506 and 508 may, in some instances, each include an instance of the ultrasonic receiver system and a portion of the light source system that are described above. In this example, the example device 500 is coupled around the wrist such that the first and the second arterial sensors 506 and 508 within the housing 502 are each positioned along a segment of the radial artery 510 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial sensors 506 and 508 are separated by a fixed distance ΔD. In some other implementations, the example device 500 can similarly be designed or adapted for positioning around a forearm, an upper arm, an ankle, a lower leg, an upper leg, or a finger (all of which are hereinafter referred to as "limbs") using a strap or band.

Figure 5B:
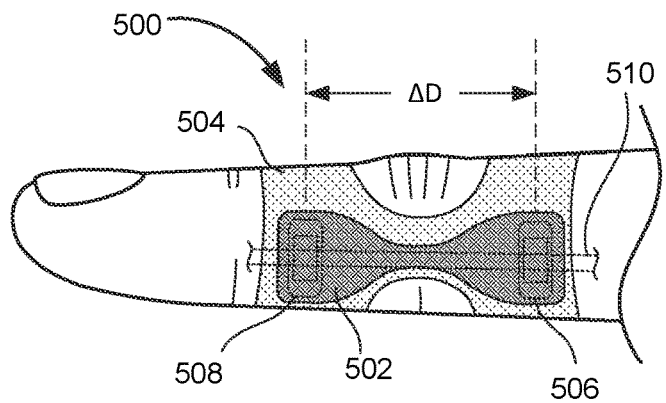
FIG. 5B shows an example monitoring device designed to be worn on a finger according to some implementations.

FIG. 5B shows an example device 500 designed to be worn on a finger according to some implementations. The first and the second arterial sensors 506 and 508 may, in some instances, each include an instance of the ultrasonic receiver and a portion of the light source system that are described above.

In some other implementations, the devices disclosed herein can be positioned on a region of interest of the user without the use of a strap or band. For example, the first and the second arterial sensors 506 and 508 and other components of the monitoring device can be enclosed in a housing that is secured to the skin of a region of interest of the user using an adhesive or other suitable attachment mechanism (an example of a "patch" monitoring device).

Figure 5C:
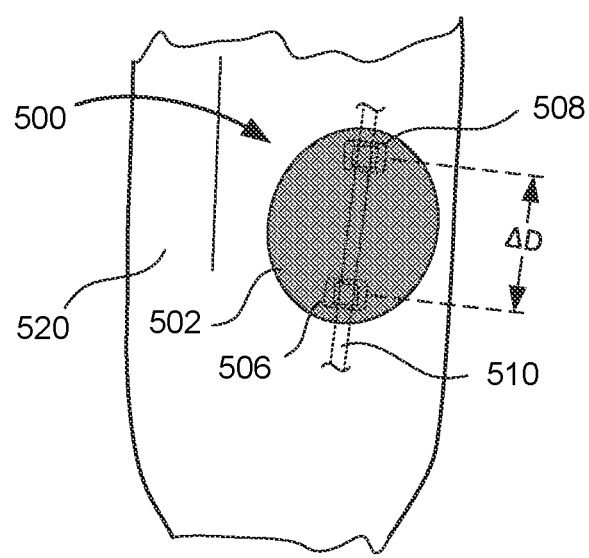
FIG. 5C shows an example monitoring device designed to reside on an earbud according to some implementations.

FIG. 5C shows an example device 500 designed to reside on an earbud according to some implementations. According to this example, the monitoring device 500 is coupled to the housing of an earbud 520. The first and second arterial sensors 506 and 508 may, in some instances, each include an instance of the ultrasonic receiver and a portion of the light source system that are described above.

Example Sensor Apparatus

As noted elsewhere, a sensor apparatus (e.g., sensor apparatus 200) may be worn at least partially by a user in order to apply pressure at different discrete pressure levels and to obtain photoacoustic signals and measurements. Such pressure applied by the sensor apparatus may be referred to herein as external pressure or externally applied pressure. In some implementations, segments of data may be collected at multiple external pressures, e.g., as applied by a cuff system 205. For example, photoacoustic signals may be acquired by the sensor apparatus (e.g., using the receiver system 202, and the light source system 204) over periods of time corresponding to the external pressures. That is, photoacoustic measurements are obtained for each pressure level to acquire information about a target object (e.g., blood vessel).

The disclosed embodiments of sensor apparatus (configured to determine artery diameter, distention, PWV, etc.) can benefit from precise counter pressure control, but operated in a completely different way compared with traditional volume-clamp and oscillometer-based methods. The PWV curves may be measured since a single point of PWV or PTT can be unreliable because of electrical noise, movement artifacts, EKG noise, respiratory events, etc. Photoacoustic waveforms and local PWV can be impacted by counter pressures applied to the artery. The curve of PWV against external pressure provides important cues for a person's blood pressure (systolic, diastolic, and mean) and blood pressure calibration information for each person.

In embodiments disclosed herein, a "closed loop" control of the pump pressure (e.g., based on feedback pressure and voltage information) can be used to control the target pressure more accurately.

Figure 6:
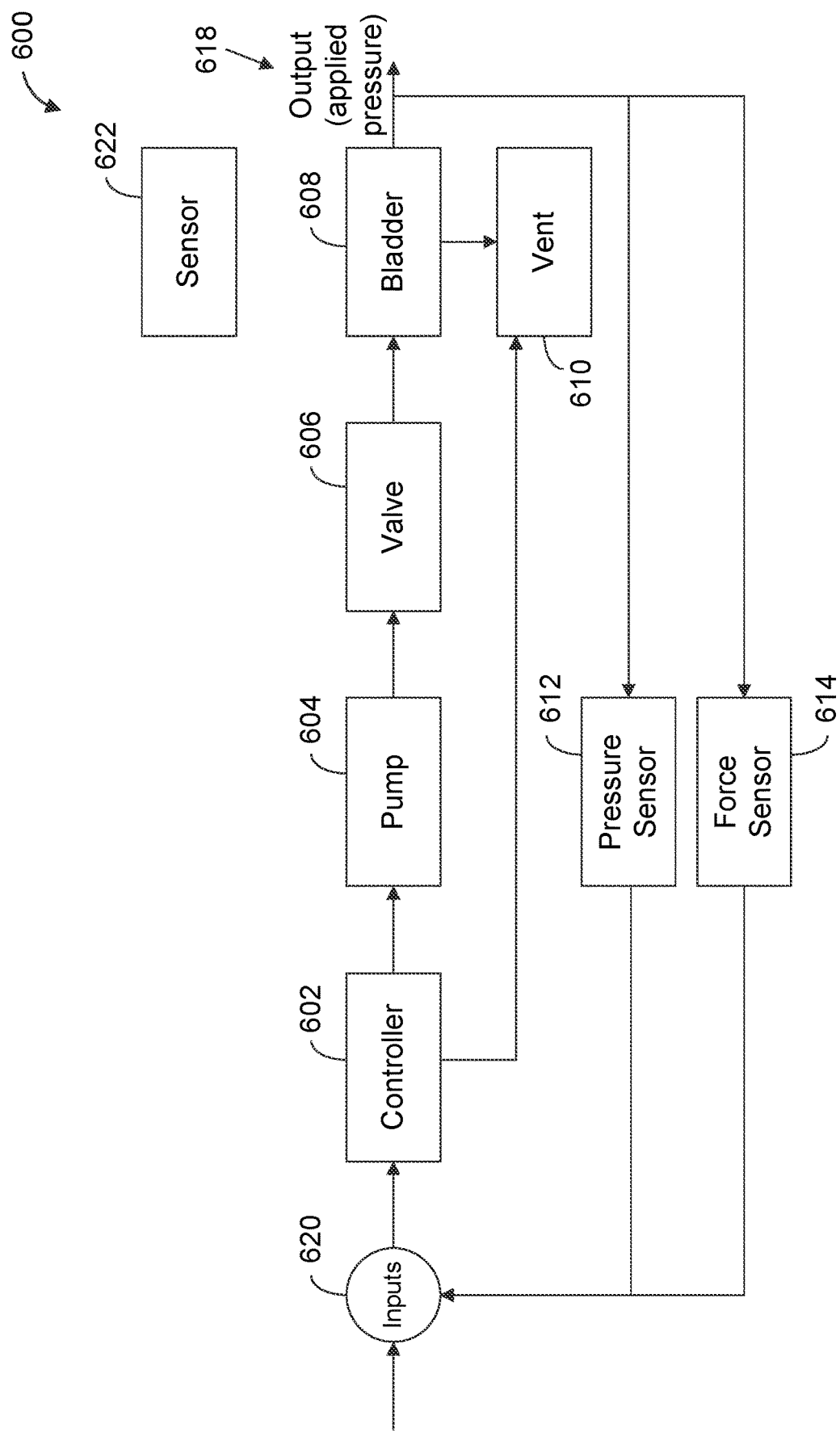
FIG. 6 is a block diagram of an example sensor apparatus, according to some embodiments.

FIG. 6 is a block diagram 600 of an example sensor apparatus, according to some embodiments. The example sensor apparatus may include, among other things, a controller 602, a pump 604, a valve 606, a bladder 608, a vent 610, and a pressure sensor 612. In some examples, a force sensor 614 may also be included. In some implementations, the controller 602 may be an example of the control system 206, while in some implementations, the controller 602 may be a separate control system capable of performing similar functionalities as the control system 206.

In some implementations, the pump 604 may be configured to flow air into the bladder 608 through the valve 606. The bladder 608 may be an airbag. The amount of air going into the bladder 608 may be based on a voltage applied by the controller 602. For example, a constant-amplitude square-wave voltage may be applied to the pump 604 (or a driver of the pump 604, embodied as, e.g., a pump drive board) until a certain applied pressure is reached, e.g., a target pressure level. This applied pressure may be generated and/or provided as an output 618, which may be used, e.g., as feedback information in a closed-loop system. During influx of air, the vent 610 may be closed (e.g., by the controller 602) to prevent air from escaping the bladder 608. The vent 610 may be opened to release air and cause the bladder 608 to deflate. In some implementations, voltage may be applied to the pump 604 to create negative pressure and remove air out of the bladder 608 until a certain pressure is reached (e.g., another target level or zero applied external pressure) rather than letting the air inside the bladder 608 come to atmospheric pressure outside the bladder 608 via an open valve.

While the vent 610 is closed, the pressure in the bladder 608 may be maintained or substantially maintained. Substantial maintenance of the pressure may refer to pressure being maintained within some degree of a target pressure, e.g., ±1 mmHg. The error range may be specific to and depend on the use case. As illustrative example values, ±2 mmHg, ±1%, ±5% or ±10% of the target pressure may be used. In some scenarios, the pressure may change over time because of a change in temperature or altitude, or a structural leak, e.g., in the valve 606. In some embodiments described below, air pressure within the bladder 608 or pressure associated with the bladder 608 may be detected by the pressure sensor 612, and the pressure information may be fed back as an input 620 to the controller 602. Pressure associated with the bladder 608 may be, for example, pressure experienced by a target object of the user close to the bladder 608, such as a blood vessel. That is, for purposes of this disclosure, the cuff pressure may be the pressure on the wall of the blood vessel. A sensor 622 (e.g., a photoacoustic sensor) may be proximate a component and may obtain biometric measurements while the pressure in the bladder 608 is maintained or substantially maintained at a target pressure level. The biometric measurements may correspond to the target pressure level. In some cases, force may be detected by the force sensor 614 not associated with air pressure within the bladder 608, e.g., force or pressure at a surface of the bladder 608, e.g., at the location of the sensor 622. This force information may also be fed back as an input 620 to the controller 602. In some cases, if there exists a strong correlation between the readings of the pressure sensor 612 and the force sensor 614, the pressure detected by the pressure sensor 612 alone may be used to determine the pressure; this could simplify the system design by having one fewer sensor.

Figure 7:
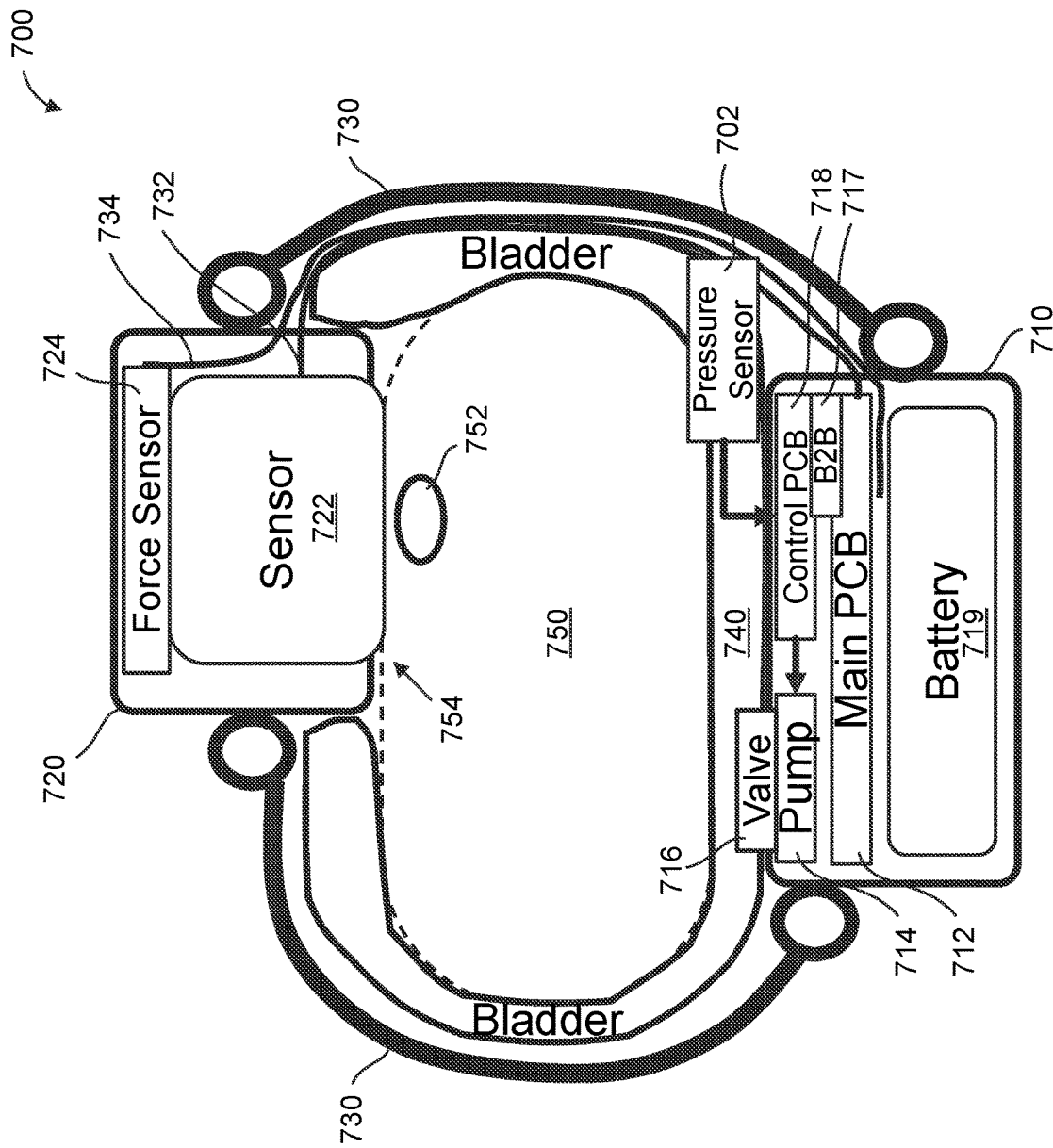
FIG. 7 depicts a cross-sectional diagram of an example structure of a sensor apparatus usable with some embodiments.

FIG. 7 is a cross-sectional diagram of an example structure of an example sensor apparatus 700 usable with some embodiments. In some embodiments, the example sensor apparatus 700 may include a pressure sensor 702 communicatively coupled with a main housing 710 and/or components of the main housing 710, a sensor housing 720, and a coupling structure 730 at least partly securing or supporting the main housing 710, the sensor housing 720, and a bladder 740. In some implementations, the coupling structure 730 may include one or more straps, bands, or other securing mechanisms. In some implementations, the coupling structure 730 may partly or completely house the aforementioned components.

In some embodiments, the example sensor apparatus 700 may be a wearable user device, where there may be space for a portion 750 of a body of a user, e.g., an appendage such as wrist, finger, arm, ankle, or leg, or other body parts conducive to wearing such as waist or neck. The portion 750 (or body part) may include a target object, such as a blood vessel 752. The example sensor apparatus 700 may be structured so as to be worn in an orientation in which that the target object (e.g., blood vessel 752) is proximate to the sensor housing 720. This way, the target object can be exposed to a sensor 722 or be in sensing range of the sensor 722 while it is active and/or skin 754 of the user is in contact with an interface associated with the sensor housing 720 or the sensor 722.

In some embodiments, the main housing 710 of the example sensor apparatus 700 may include a main board 712, which may be a printed circuit board (PCB) having control components, e.g., logic, controller, memory, and/or storage with instructions. The main housing 710 may further include a pump 714 and at least a portion of a valve 716, the pump 714 coupled to the valve 716, the valve 716 interfacing with the bladder 740 to provide an inlet and outlet for air. In some implementations, the main housing 710 may further include a control board 718, which may be another PCB having control components, e.g., logic, controller, memory, and/or storage with instructions. In some implementations, the control board 718 may be coupled to the main board 712 via a board-to-board interface 717. The main housing 710 may further include a power source, such as a battery 719. The battery 719 may power one or more components of the main housing 710, such as the pump 714, the valve 716, the main board 712, the control board 718, or a combination thereof.

In some configurations, the main board 712 or the control board 718 may generate a control signal. The control signal may be configured to cause a voltage corresponding to a prescribed pressure level to be applied to the pump 714. More specifically, in some configurations, DC (direct current) voltage applied to pump control circuitry during a pressurization process may generate a constant-amplitude square wave to drive the pump. Target pressure and air flow rate are proportional to the applied DC voltage. A passive check value may open or close the air path of an inlet, an outlet, or an exhaust hole, and may be in a fixed position during inflate and deflate operations. Removing power from the pump may open the outlet and exhaust path and cause deflation of the bladder during an exhaust process.

Figure 8:
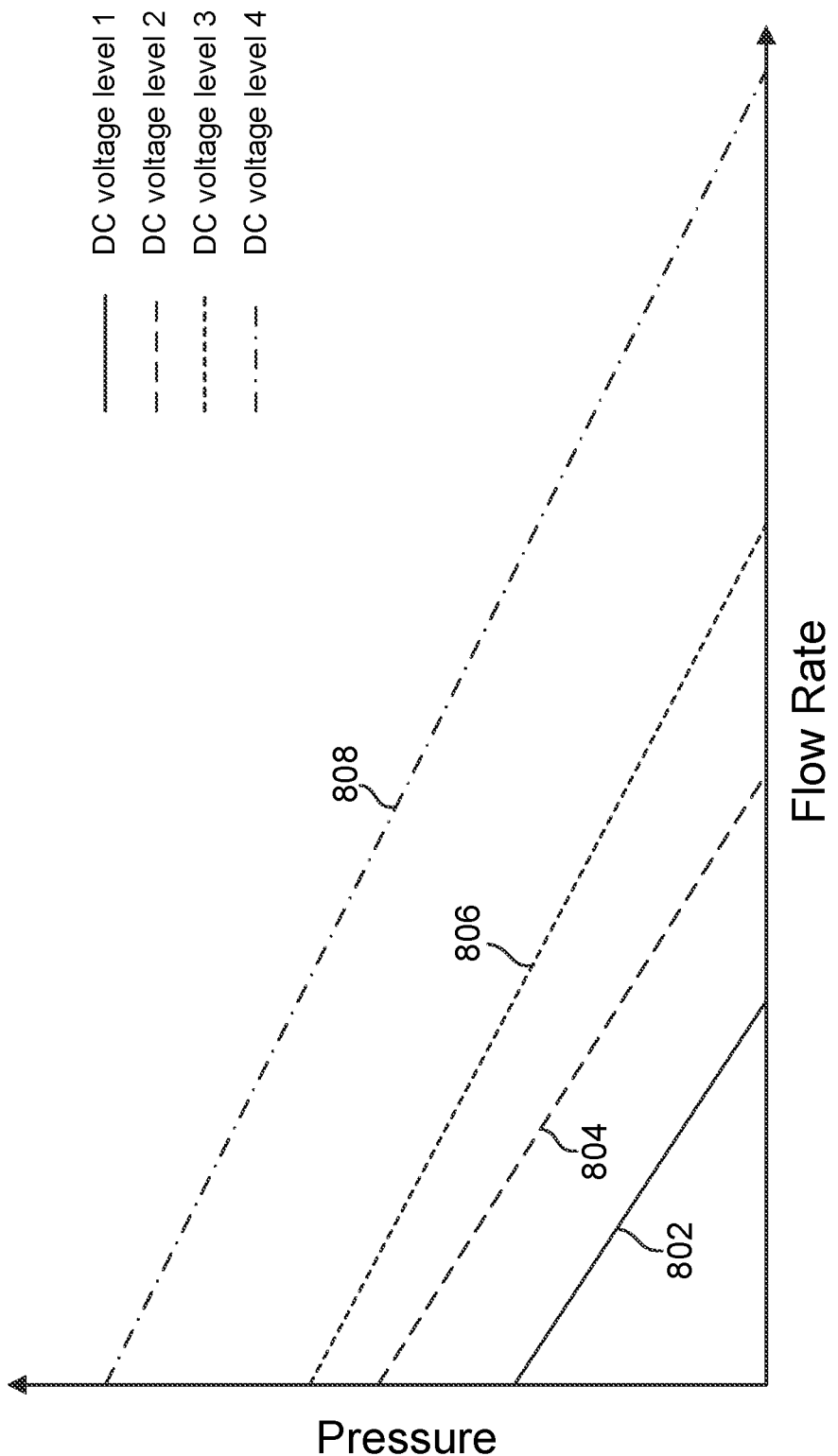
FIG. 8 shows example characteristic curves of pressure with respect to flow rate at different voltages applied to a pump of a sensor apparatus disclosed herein.

Briefly referring to FIG. 8, example characteristic curves of resulting pressure with respect to flow rate at different voltages applied to a pump of a sensor apparatus disclosed herein are shown. For instance, when pressure reaches the target pressure, flow rate becomes zero. Curve 802 represents pressure with respect to flow rate at a first voltage level. Curve 804 represents pressure with respect to flow rate at a second voltage level. Curve 806 represents pressure with respect to flow rate at a third voltage level. Curve 808 represents pressure with respect to flow rate at a fourth voltage level. Each curve being linear represents how proportional the target pressure and air flow rate are, as noted above. Moreover, it can be seen that pressures and flow rates can differ depending on the voltage applied. In the depicted curves, the second voltage level may be higher than the first, the third higher than the second, and the fourth higher than the third. While other voltage levels are possible, illustrative example values for these voltages levels may be 8 V for the first voltage level, 11 volts for the second voltage level, 13 volts for the third voltage level, and 16.5 volts for the fourth voltage level.

Returning to FIG. 7, in some implementations, the board-to-board interface 717 may provide a data connection to provide signals to the pump 714 via the control board 718. In some embodiments, the pressure sensor 702 may detect pressure inside the bladder 740. Pressure information may be provided (fed back) to the control board 718 (or main board 712), which may determine the voltage to be applied to the pump 714. The new pressure may in turn be detected by the pressure sensor 702, resulting in a feedback loop of the pressure sensor 702, the pump 714, and the bladder 740 (and/or a vent to release air, not shown).

In some embodiments, the sensor housing 720 may include a sensor 722. In some configurations, the sensor 722 may be a biometric sensor, such as a photoacoustic sensor. As alluded to above, the biometric sensor may additionally include other types of sensors, e.g., a PPG sensor. In some embodiments, the sensor housing 720 may also include a force sensor 724. In some configurations, the main housing 710 and the sensor housing 720 may be electrically coupled by a first bus 732 between the main board 712 and the sensor 722. In some cases, the first bus 732 may be between the control board 718 and the sensor 722. The first bus 732 may communicate control signals configured to operate the sensor 722 and/or data signals relating to measurements taken by the sensor 722. For instance, the photoacoustic sensor may obtain photoacoustic data from the blood vessel 752 at one or more times while the skin 754 of the portion 750 is in contact with the sensor housing 720 at one or more external pressure levels applied by the bladder 740. As will be illustrated in FIG. 9, the one or more external pressure levels may be discrete pressure levels at corresponding times with transition portions between, appearing like a staircase as discussed below. This photoacoustic data may be sent to the main board 712 and/or the control board 718, where the data may be stored at a memory. In some configurations, the main housing 710 and the sensor housing 720 may be electrically coupled by a second bus 734 between the force sensor 724 and the main board 712 (or the control board 718) to exchange control signals and/or measurements taken by the force sensor 724. The first bus 732 and/or the second bus 734 may be configured to deliver power to the components of the sensor housing 720.

Figure 9:
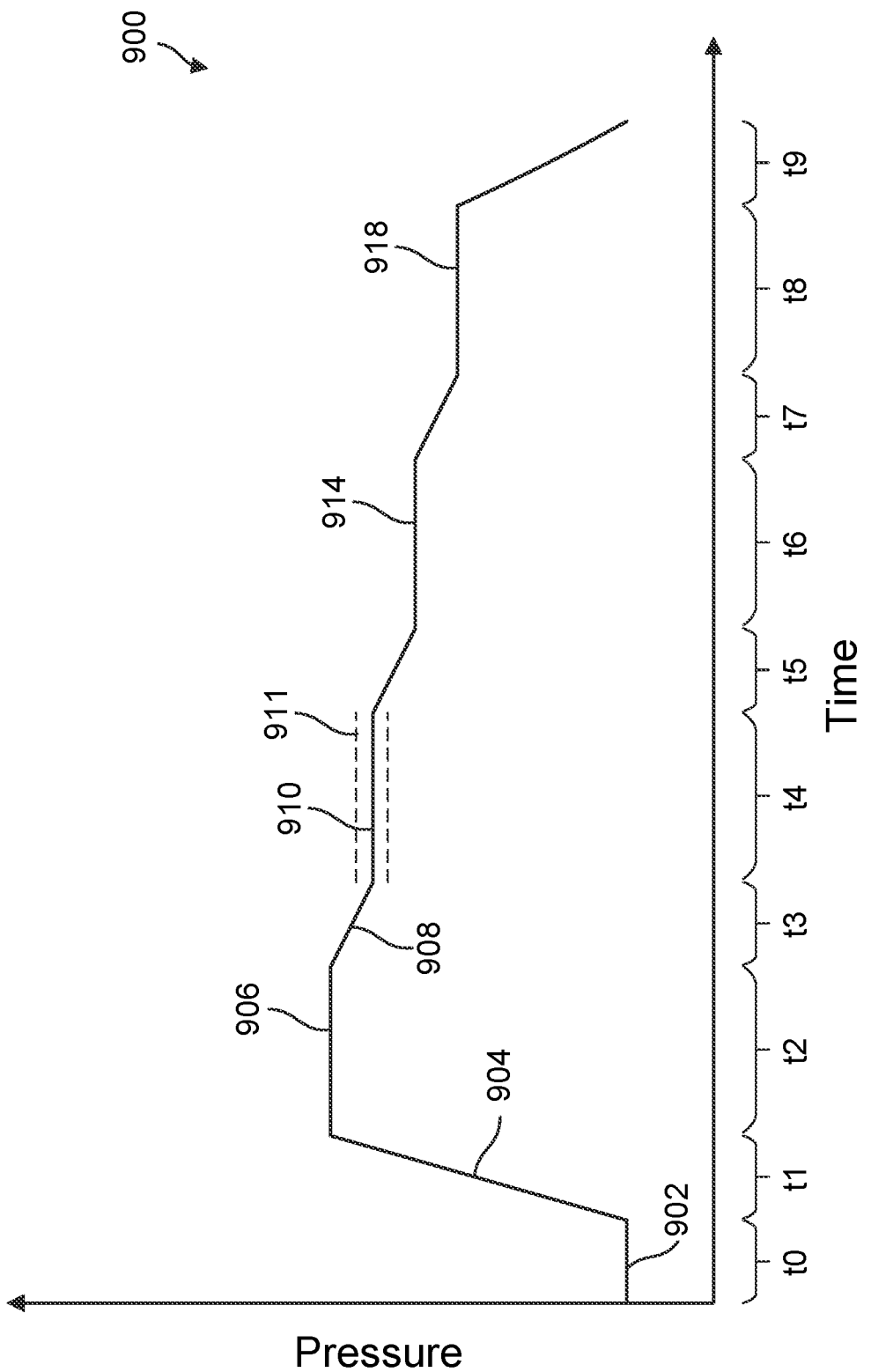
FIG. 9 is a graph of an example of staircase pressure levels that can be applied using a sensor apparatus disclosed herein.

FIG. 9 is a graph 900 of an example of staircase pressure levels that can be applied using a sensor apparatus disclosed herein. In this example, during time t0, a bladder or airbag may be at an initial pressure level 902, e.g., applying an external pressure of 0 mmHg. No voltage may be applied to a pump associated with the bladder. The bladder may be an example of the bladder 740 and part of a cuff system 205 of a sensor apparatus 200.

During a transition portion 904 at time $t_1$, the external pressure being applied by the bladder may increase toward a pressure level 906. The pressure may be increased by flowing air into the bladder via a corresponding voltage applied to the pump while the vent is closed until the pressure reaches the next pressure level 906. Pressure level 906 may be considered a target pressure level for the duration of time $t_2$. At a subsequent time $t_3$, the pressure may decrease toward pressure level 910 during a transition portion 908. The pressure may be decreased by opening the vent until the pressure reaches the next pressure level 910 during time $t_4$. In some configurations, the pressure may be decreased by applying a voltage to the pump to cause negative pressure and air to be removed from the bladder. Similar to pressure level 906, pressure level 910 may be a target pressure level for the duration of time $t_4$. In the example illustrated by graph 900, external pressure levels such as pressure levels 906 and 910 may be discrete pressure levels at corresponding times with transition portions between, appearing like a staircase. Pressure levels 914 and 918 are further examples of the discrete pressure levels. The pressure levels may continue in a similar fashion during times $t_5$ to $t_9$ until the pressure reaches back to the initial pressure level 902 (e.g., 0 mmHg).

Example ranges of the discrete applied external pressure levels may be 20-90 mmHg or 20-50 mmHg. Other pressure levels or ranges that are deemed comfortable to the user, including during sleep for overnight biometric measurements, may be applied. Each of the discrete pressure levels may be held at a constant level or a substantially constant level. That is, the pressure may have an error or range of, e.g., ±1 mmHg. The error range may be specific to and depend on the use case. As illustrative example values, ±2 mmHg, ±1%, ±5% or ±10% of the target pressure may be used. An example error range for one pressure level 910 is depicted by range 911.

Figure 9A:
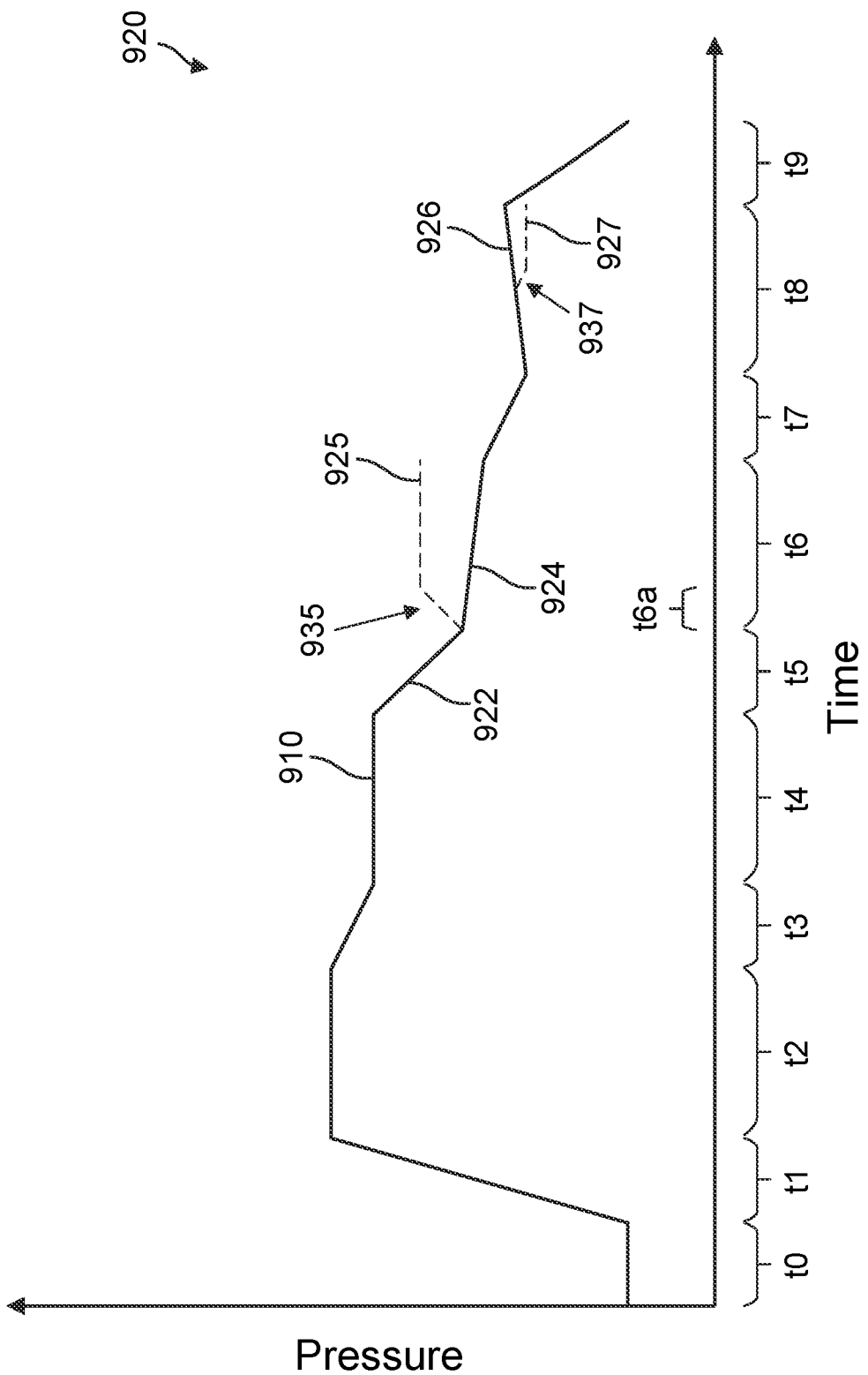
FIG. 9A is a graph of another example of staircase pressure levels that can be applied using a sensor apparatus disclosed herein.

FIG. 9A is a graph 920 of another example of staircase pressure levels that can be applied using a sensor apparatus disclosed herein. It may a continuation of the graph 900 from the end of $t_4$, except that conditions may be different. Temperature or altitude may be different, for example, causing deviations in target pressure levels. As an example, at transition portion 922 during $t_5$, the pressure applied by the bladder decreases from a previous pressure level 910 to a target pressure level 924. However, because of lower temperature or higher altitude, for example, compared to when the pressure of the bladder increased, the drop in pressure during $t_5$ is more pronounced than previous drops in pressure during a typical transition period or a previous transition period (e.g., $t_3$). Moreover, the target pressure level 924 may drift downward rather than stay constant or substantially constant, which may again be as a result of the lower temperature or higher altitude. As will be discussed below, in such cases, the pressure can be detected by a pressure sensor and become known by a controller or control board, which can in some cases compensate for the lower pressure and restore the pressure to the intended target pressure level (e.g., alternate pressure level 925). This change may occur by applying an appropriate voltage to the pump during time $t_{6a}$ to bring the pressure to the intended target pressure level.

During time $t_7$, the pressure may decrease by the normal amount as other transition periods. However, during time $t_8$, pressure level 926 may increase rather than stay constant or substantially constant. This could be due to, e.g., prolonged pump operation, or higher temperature or lower altitude compared to before. However, this higher pressure may be detected by a pressure sensor and become known by a controller or control board, which can in some cases compensate for the higher pressure and restore the pressure to the intended target pressure level (e.g., alternate pressure level 927). Alternate pressure levels 925, 927 may have their own respective transitions 935, 937 associated therewith, during which noise-sensitive measurements may not be taken.

In graphs 900 and 920, the goal is to have discrete pressure levels at constant or substantially constant pressure levels, during which sensor measurements may be obtained. In some approaches, in the case of photoacoustic measurements, a photoacoustic sensor may operate and obtain photoacoustic measurements only during the discrete pressure levels, and the photoacoustic sensor may not obtain photoacoustic measurements during transition periods (including those that compensate for unintended pressure changes, e.g., during time $t_{6a}$), because the pump and/or valve (proximate the photoacoustic sensor) may create noise during times of inflation and deflation, and the noise may interfere with noise-sensitive photoacoustic measurements. The pump operation may stop during photoacoustic measurements while the target pressure is maintained in the bladder.

Example Pressure Control Systems

One salient aspect of the sensor apparatus discussed throughout this disclosure is that it can provide discrete, precisely controlled target pressure levels using the sensor apparatus. As noted elsewhere, in some embodiments, the sensor apparatus may include at least a photoacoustic sensor that obtains photoacoustic measurements from a target object while a cuff system applies a pressure. It is desirable for this pressure to be accurate to the desired target pressure level in order to obtain an accurate correlation between pressure and measurements (and derived characteristics of the target object, such as PWV associated with a blood vessel). Obtaining accurate measurements and key characteristics such as PWV allows useful input parameters for estimation of valuable parameters such as blood pressure. To these ends, various approaches for controlling pressure and compensating for pressure changes are described herein.

Figure 10:
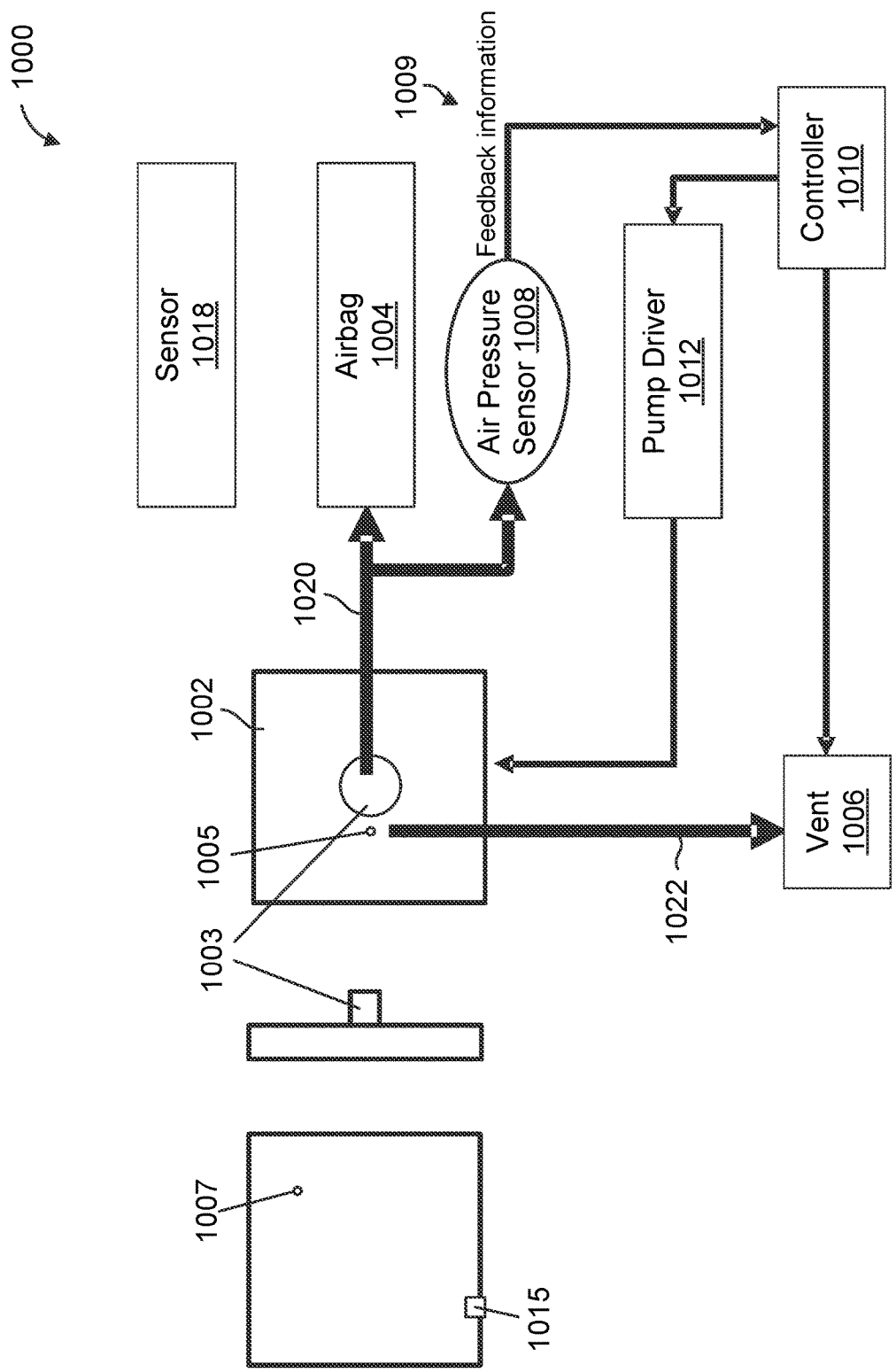
FIG. 10 is a block diagram of an example sensor apparatus according to some embodiments.

FIG. 10 is a block diagram of an example sensor apparatus 1000 according to some embodiments. The example sensor apparatus 1000 may be an example of the example sensor apparatus of FIG. 6 or the example sensor apparatus 700 of FIG. 7. In some embodiments, the example sensor apparatus 1000 may include a pump 1002. The pump 1002 may be connected to an airbag 1004 (also referred to as a bladder herein) and provide air through an air discharge port or nozzle 1003 of the pump 1002, and to a vent 1006 via an exhaust port 1005 of the pump 1002. Air may be received through air intake hole(s) 1007 and flow into the airbag 1004 (based on positive voltage) via a tube 1020, or stop flowing in (with zero voltage) based on a control signal (providing an on/off effect to the pump 1002) generated by the controller 1010 of the example sensor apparatus 1000. The control signal may be sent to a pump driver 1012, which may provide a corresponding voltage for a target pressure level to the pump 1002. In some configurations, the pump driver 1012 may be part of the pump 1002. A constant power (DC voltage) may be applied to the pump 1002. In some implementations, the pump driver 1012 may be an example of control board 718. The controller 1010 may also send a control signal to the vent 1006 to open or close during inflation or deflation of the airbag 1004. For example, the vent 1006 may be closed while the pump 1002 is inflating the airbag 1004, and may be opened to deflate the airbag 1004. In some variants, the pump 1002 may have structural features such as external terminal(s) 1015.

In some embodiments, a closed loop may be employed by the example sensor apparatus 1000. A pressure sensor 1008 may detect pressure of the air inside the airbag 1004 or the pressure of the air going into the airbag 1004. The pressure information 1009 may be sent as feedback information to the controller 1010. Based on the pressure information and the target pressure level (e.g., a comparison or difference between the two pressures), the controller 1010 may adjust the voltage provided to the pump 1002, thereby effectuating a feedback loop. One goal of the feedback loop may be to minimize the difference between the difference between the feedback pressure and the target pressure. A biometric sensor 1018 (e.g., a photoacoustic sensor) may be proximate a component and may obtain biometric measurements while the pressure in the airbag 1004 is maintained or substantially maintained at a target pressure level. The biometric measurements obtained may thus correspond to the target pressure level.

Example operations involving the example sensor apparatus 1000 may include one or more of the following. (1) The vent 1006 may be closed, and the airbag 1004 may be inflated (e.g., by applying a voltage to the pump 1002, e.g., a constant-amplitude square-wave voltage). The voltage may correspond to a target pressure level applied by the airbag 1004 to a portion of a user.

(2) When the airbag 1004 is inflated to the target pressure level (detected and output by the pressure sensor 1008), the voltage applied to the pump 1002 may be reduced to zero. The pump 1002 is off in this state. In some cases, the exhaust port 1005 may be opened to a tube 1022. It can be assumed that air is not leaking from the airbag 1004 since the vent 1006 is closed at this time and the pressure in airbag 1004 is maintained.

Pressure and corresponding voltage may be correlated based on a calibration performed prior to use of the example sensor apparatus 1000, with a predetermined relationship being predetermined between pressure and voltage. For instance, pressure and voltage data may be previously measured and stored in a data structure, such as a look-up table, list, matrix. This predetermined relationship may be used to bring the pressure to the target pressure level accordingly. Examples of these pressure drops and rises are shown in FIG. 9A. Examples voltages and corresponding flow rates of air for a pressure level in the airbag 1004 are shown in FIG. 8.

(3) Sensor measurements may be made with respect to a target object while the pump 1002 is off and the airbag 1004 is at target pressure level, e.g., photoacoustic measurements from a blood vessel of the user. In some implementations, pressure in the airbag 1004 is increased to the target pressure level if the pressure drops between measurements or relative to the target pressure level; pressure may be decreased to the target pressure level if the pressure increases between measurements or relative to the target pressure level. These inadvertent rises or drops in pressure may be caused by changes in condition(s) such as temperature or altitude. For example, the temperature may have dropped and reduced the pressure, or the temperature may have increased (e.g., at least partly due to higher temperature or prolonged operation of the sensor apparatus). The pressure may be monitored by the pressure sensor 1008 and provided to the controller 1010 as pressure information at predetermined frequencies, e.g., every 0.005 second, 0.1 second, 0.5 second. The frequency of detection may depend on the error range (e.g., ±1 mmHg).

(4) The airbag 1004 may be inflated or deflated to a new target pressure level. If the new target pressure level is greater than the current pressure level set by the previous target pressure level, power may be provided to the pump 1002 to turn it on while the vent 1006 is closed until the new target pressure level is reached. If the new target pressure level is lower than the current pressure level set by the previous target pressure level, the vent 1006 may be opened until the pressure drops below the new target pressure level, and then, power may be provided the pump 1002 to turn it on while the vent 1006 is closed until the new target pressure level is reached. In another approach, the vent 1006 may be opened until the pressure drops directly to the previous target pressure level. While this approach may save power, it may be less accurate than dropping the pressure below the new target pressure level and increasing it to the new target pressure level. While the airbag 1004 is being inflated or deflated, no photoacoustic measurements (or other sensing modalities involving acoustic signals, such as a microphone or an ultrasound receiver) may be taken to mitigate noise interference. However, in some cases, other types of sensors may be active, such as an optical sensor (e.g., PPG sensor).

Hence, the above example operations use a feedback loop of pressure information (e.g., to maintain a constant or substantially constant pressure at the target pressure level of the airbag 1004) so that the externally applied pressure is known, precise across measurements, and can be correlated to the sensor measurements taken. Pressure information may indicate a deviation from a target pressure level (e.g., as a result of temperature or altitude changes) or a difference between a current target pressure level and the next target pressure level. During the changes in pressure levels, the example sensor apparatus 1000 may stop taking certain measurements to avoid noise interference.

Figure 11:
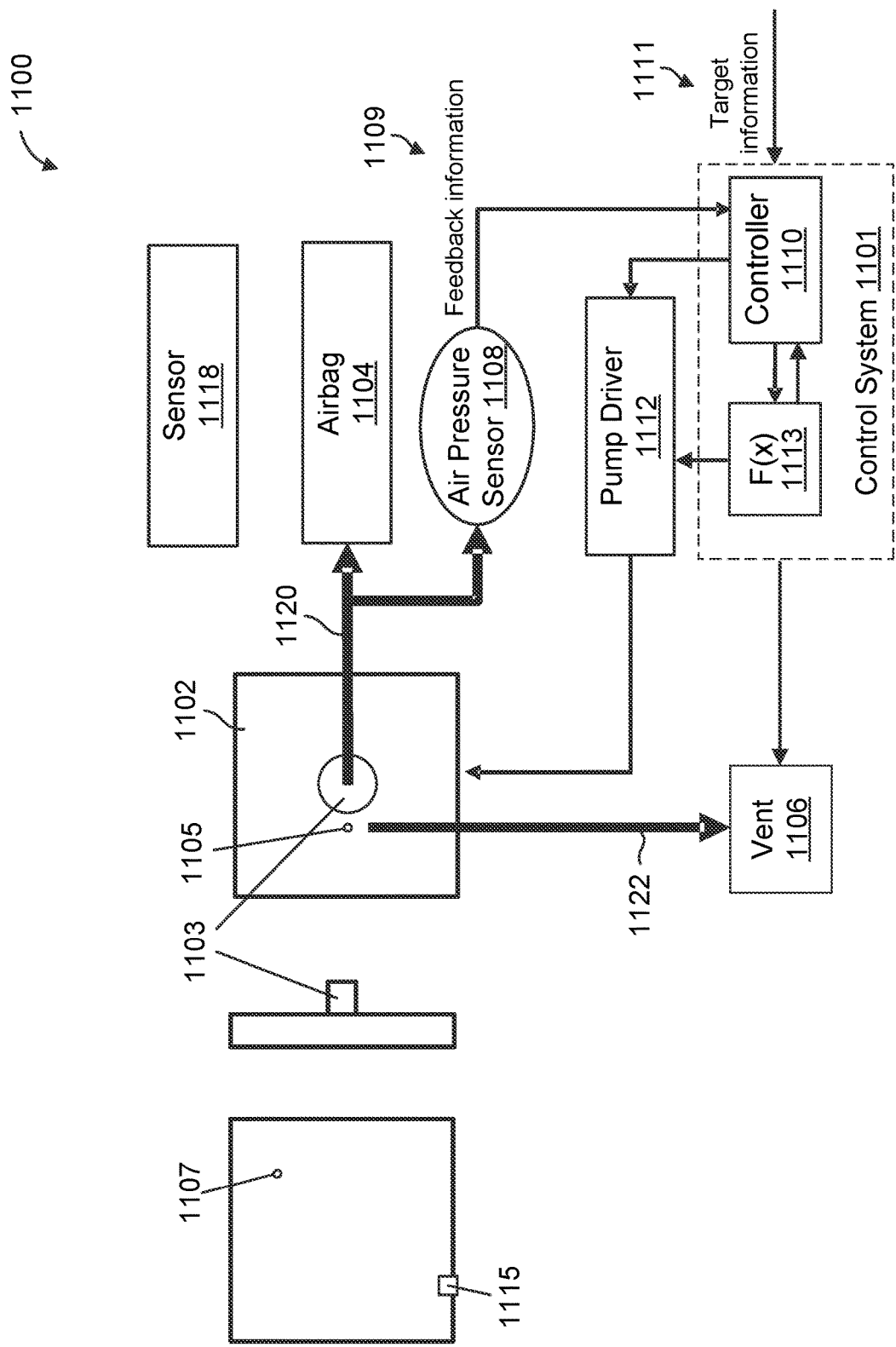
FIG. 11 is a block diagram of another example sensor apparatus according to some embodiments.

FIG. 11 is a block diagram of an example sensor apparatus 1100 according to some embodiments. The example sensor apparatus 1100 may be an example of the example sensor apparatus of FIG. 6 or the example sensor apparatus 700 of FIG. 7. In some embodiments, the example sensor apparatus 1100 may include at least a pump 1102, an airbag 1104, an air discharge port or nozzle 1103, an exhaust port 1105, a vent 1106, air intake hole(s) 1107, a pump driver 1112, a pressure sensor 1108, structural features such as external terminal(s) 1115, a sensor 1118 (e.g., a photoacoustic sensor) proximate a component, and tubes 1120 and 1122. These components may be similar to or examples of their counterparts described with respect to FIG. 10, and their descriptions will be omitted for brevity.

The example sensor apparatus 1100 may include a control system 1101 including a controller 1110. The control system 1101 and/or its component(s) may be configured to generate and send a control signal (providing an on/off effect to the pump 1102 and/or to open or close the vent 1106 during inflation or deflation of the airbag 1104), similar to controller 1010. However, control system 1101 and/or controller 1110 may include additional features.

In some implementations, control system 1101 and/or controller 1110 may be configured to implement additional logic, such as fuzzy logic 1113. Fuzzy logic may refer to computing based on degrees rather than a binary or Boolean-type true-or-false (1 or 0) logic. A system using fuzzy logic having more than two levels or states may have so-called membership values or so-called degrees of membership within a so-called fuzzy set. Examples of a fuzzy set may be {large positive, medium positive, small, medium negative, large positive} and {certainly yes, possibly yes, cannot say, possibly no, certainly no}. Each member of the fuzzy set may have a membership function that increases or decreases with respect to an input or variable. That is, fuzzy logic may consider states between 0 and 1 depending on the degree of a characteristic, and more closely resembles granular (human-like) reasoning. A system implementing fuzzy logic can achieve a faster response to changes in condition (e.g., temperature), result in a smaller overshoot or undershoot of the response, and better overall tracking and performance, as the fuzzy logic can provide decision making based on a wide variety of input, whether it is imprecise, distorted, or noisy input information. Moreover, controllers using fuzzy logic are inherently nonlinear controllers that can handle time-varying systems such as control systems of the type shown in FIGS. 11 and 12.

In some approaches, an output of the fuzzy logic 1113 may include a voltage value provided to the controller 1110 and/or control signal for the pump driver 1112 or the vent 1106, associated with a desired pressure to be applied. The voltage value and/or the control signal may indicate or adjust the current pressure level by comparing feedback information 1109 from the pressure sensor 1108, and target information 1111 input to the control system 1101.

Figure 11A:
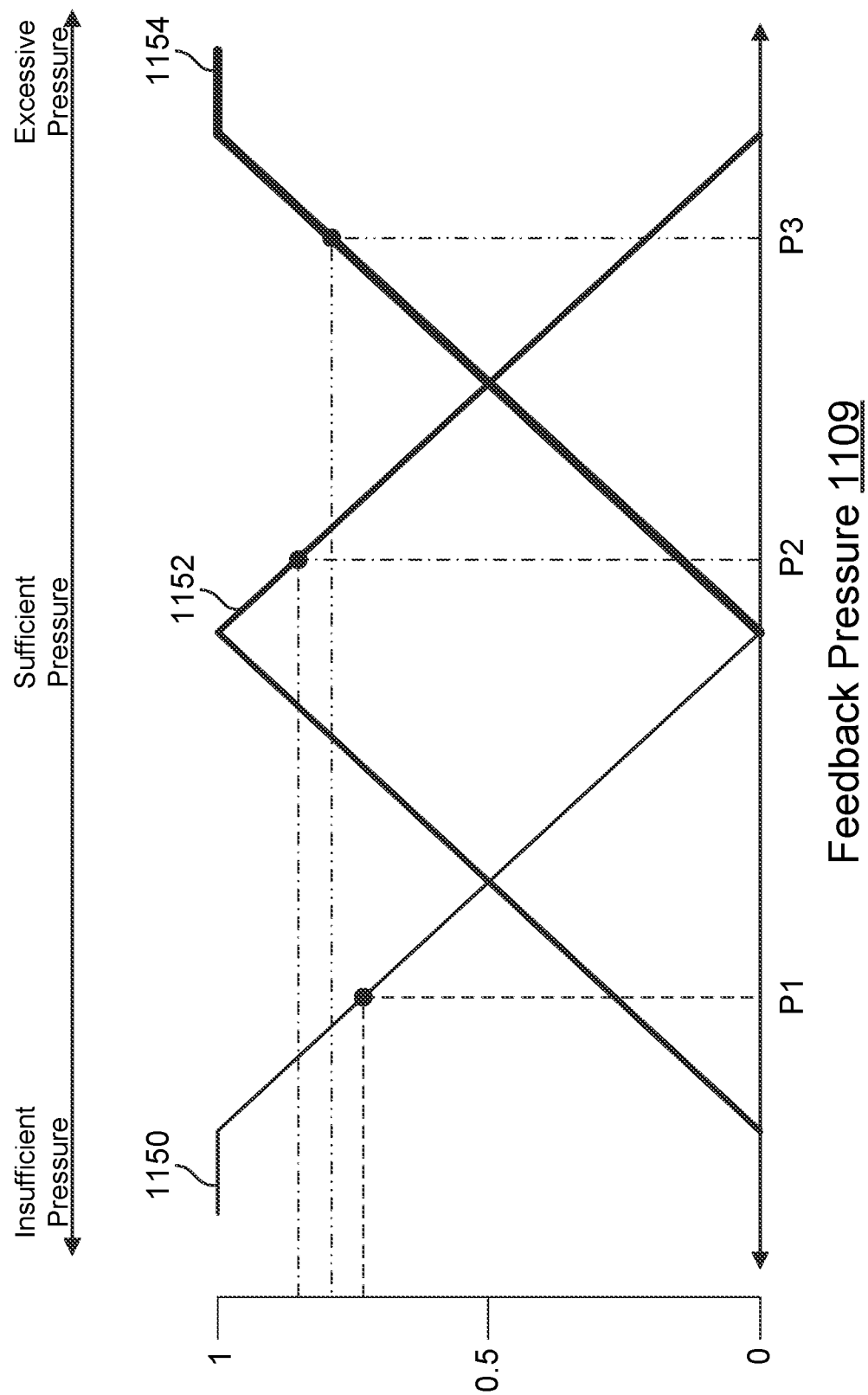
FIG. 11A shows examples of membership functions applied by a fuzzifier, useful for implementing fuzzy logic with the example sensor apparatus of FIG. 11.

Examples of membership functions 1150, 1152, 1154 useful for implementing fuzzy logic are shown in FIG. 11A. More specifically, FIG. 11A shows membership functions 1150, 1152, 1154 applied by a trapezoidal or triangular fuzzifier. A first membership function 1150 may be associated with insufficient pressures, a second membership function 1152 may be associated with sufficient pressures, and a third membership function 1154 may be associated with excessive pressures. In FIG. 11A, these membership functions 1150, 1152, 1154 can be distinguished by the respective thickness of the lines. Membership functions may not necessarily have a peak or linear relationships as shown; e.g., there may be varying slopes or curves or plateaus along the function in some cases.

A system using fuzzy logic may include four components: a fuzzifier (taking an input), a rule base, an inference engine, and a defuzzifier (providing the output). The fuzzifier can receive as input the feedback information 1109 from the from the pressure sensor 1108. Based on the feedback information 1109 and a rule base, the inference engine can determine whether the pressure in the airbag 1104 is "insufficient," "sufficient," "excessive," as illustrative examples, or somewhere in between two of the foregoing states, which can inform the significance of the pressure in the airbag 1104 and any action needed (e.g., change in pressure or associated voltage). The significance of the determined state can be decided by a defuzzification process, which can result in an output such as a control signal to be sent to the pump 1102 or the vent 1106.

In one example scenario in the FIG. 11A example, a pressure of P1 may be received by the fuzzifier. P1 may correspond to approximately 0.75 along the first membership function 1150, indicating that the pressure is "pretty low," as it is relatively high along the first membership function 1150 and between "insufficient" and "sufficient." Another way to interpret 0.75 is that there is a 75% probability that the input pressure is insufficient. P1 may also correspond to approximately 0.25 along the second membership function 1152 and 0.00 along the third membership function 1154. A fuzzy variable of [0.75, 0.25, 0] can thus be determined. A rule set from the rule base could indicate that if a pressure is above 0.5 along a membership function, and the target pressure is above the input pressure (e.g., P¬1), then the pressure should be increased. The fuzzy logic 1113 can thus output and send a control signal to apply a corresponding voltage that drives the pump 1102 to inflate the airbag 1104.

In another example scenario, a pressure of P2 may be received. According to an example rule set that requires 0.75 or greater along a membership function 1152, it may be determined that no change in pressure is necessary. However, if an example rule set requires 0.95 or greater along a membership function 1152 and the target pressure is lower, it may be determined that P2 is too high. In such a case, a control signal may be generated which opens the vent 1106 to deflate the airbag 1104 and/or activates the pump 1102 with a voltage that would bring the pressure to the target pressure.

In another example scenario, a pressure of P3 may be received. Similar to the above examples, this pressure may be deemed excessive (or not) depending on the rule set and the target pressure level 1111.

In some implementations, the fuzzy logic 1113 can be implemented with a neural network 1130, e.g., an artificial neural network (ANN) or a radial basis function (RBF) network, to produce a self-learning model. In some configurations, the neural network 1130 may include an input layer, a fuzzy layer, a fuzzy inference layer, and an output layer. In other configurations, the neural network 1130 may include more layers or fewer layers. For instance, a hidden layer with a nonlinear RBF activation function may be implemented between the input layer and the output layer. Hence, the fuzzy logic 1113 may benefit from not only granular outputs that mimic human decision making on whether and how to control the pressure applied by the example sensor apparatus 1100, but also self-learning using the neural network 1130 to further refine the outputs.

Figure 11B:
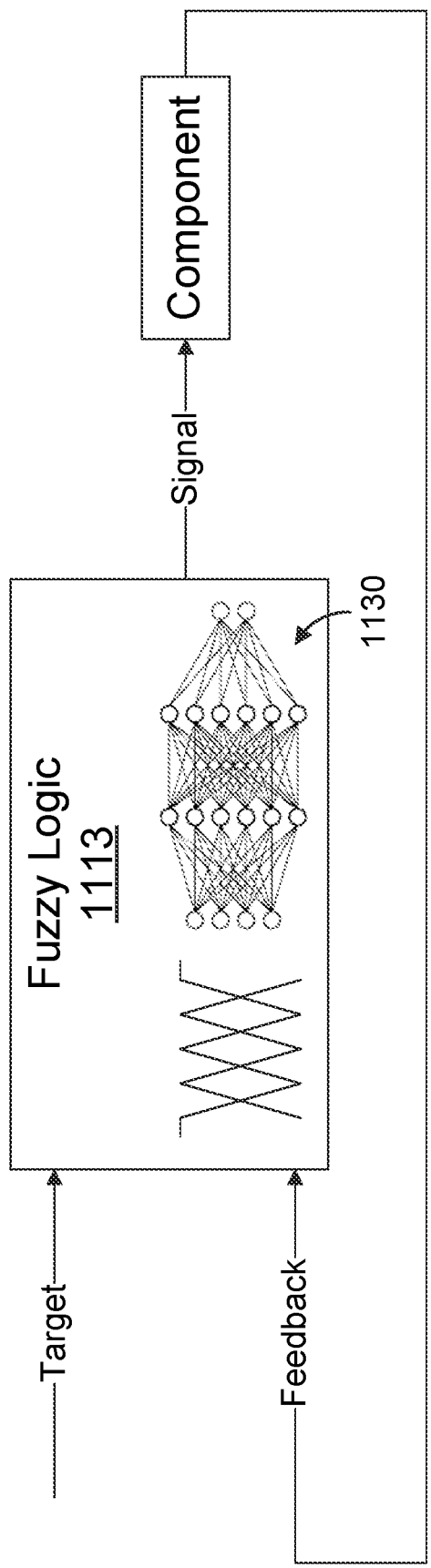
FIG. 11B illustrates a simplified block diagram of how the fuzzy logic receives target information and feedback information and produces a control signal.

FIG. 11B illustrates a simplified block diagram of how the fuzzy logic 1113 receives target information 1111 and feedback information 1109 (e.g., from a component of the example sensor apparatus 1100, such as the pressure sensor 1108) and produces a control signal for the component. This can enable granular, "fuzzy," and human-like reasoning as to whether and how to adjust the pressure in the airbag 1104.

The above examples are purely illustrative of an approach that could be taken using feedback pressure information 1109 and fuzzy logic 1113 to adjust the pressure as necessary. Holding the pressure at a particular pressure level is important for the estimation of physiological parameters such as blood pressure using sensor measurements. Other types of fuzzifiers that can be used by the controller 1110 may include a Singleton fuzzifier or a Gaussian fuzzifier.

Figure 11C:
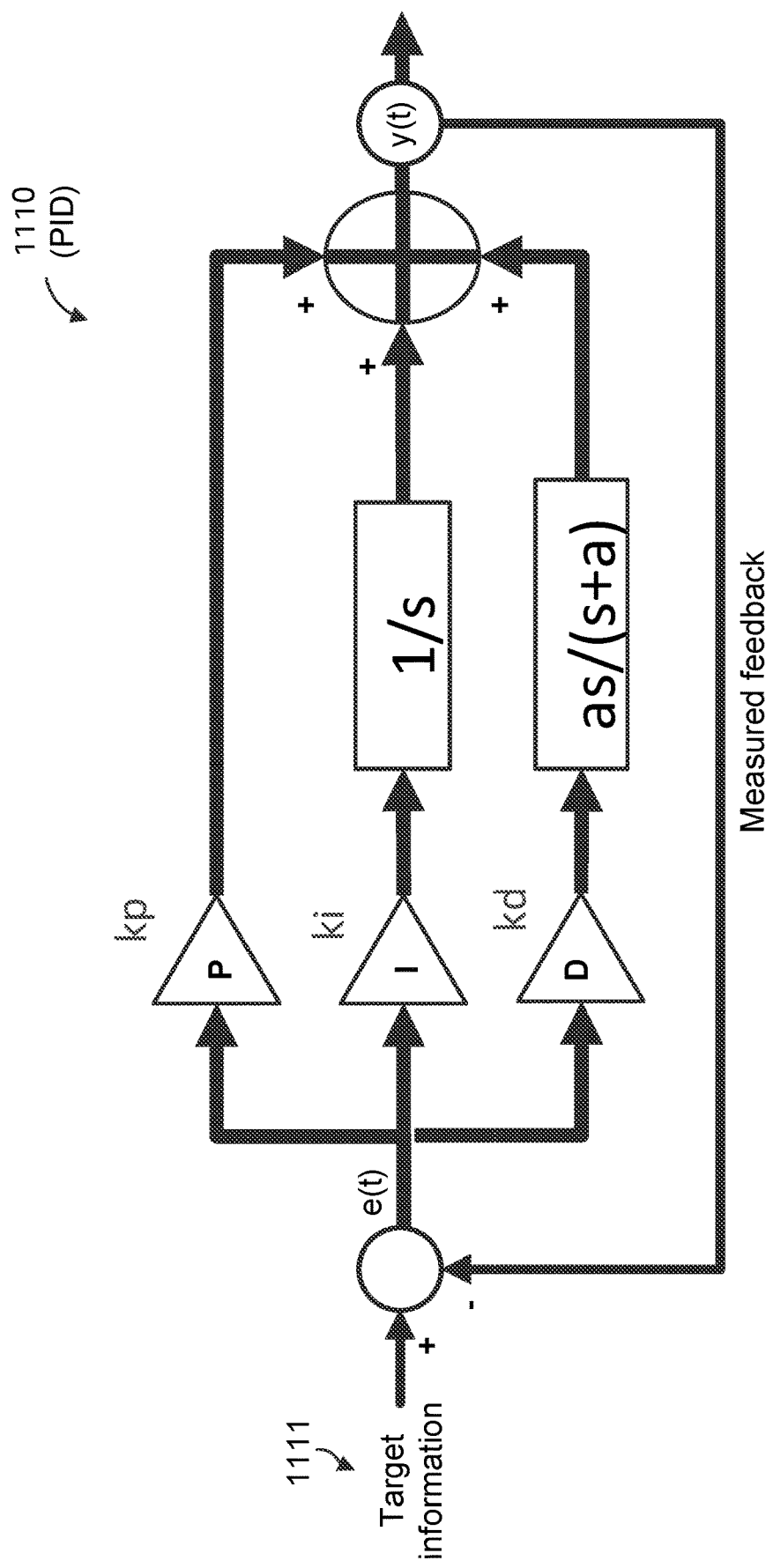
FIG. 11C is a block diagram of a proportional-integral-derivative (PID) controller in a feedback loop, useful with the example sensor apparatus of FIG. 11.

In some implementations, control system 1101 may be or include a proportional-integral-derivative (PID) controller, and controller 1110 may be a PID controller. A PID controller can be used in a control-loop mechanism that uses feedback, which is useful for control systems. FIG. 11C is a block diagram of a PID controller in a feedback loop. PID controllers are robust, simple to design and retune parameters, and capable of showing a clear relationship among system parameters. PID controllers are designed to handle linear control systems with stability and response dynamics, and its parameters can be tuned via an iterative procedure or other metaheuristic methods. The utility of PID controller is based on accuracy of system models and variables.

A PID controller can use three control terms having proportional (P), integral (I), and derivative (D) influence on the output to apply accurate and optimal control. Term P is proportional to the error e(t), the difference between a desired target (e.g., based on target information 1111) and the measured output of a process y(t). Gain factor Kp is proportional to the size of the error e(t). Term I is based on an integration of past values of the error e(t) over time, which accounts for historic cumulative value of the error. Factor Ki adds a control effect that seeks to eliminate residual error. Term D is an estimate of the future trend of the error e(t) based on current rate of change. Factor Kd seeks to reduce or damp the effect of the error e(t), where the more rapid the change, the greater the control effect. The effects produced by the three terms are balanced by tuning a control loop to produce an optimal control function.

In some implementations, controller 1010 of FIG. 10 may implement one or more of the above features of controller 1110 as well (e.g., fuzzy logic, neural network, or PID controller). In this way, pressure may be better controlled in the airbag 1004 without using calibrated rules.

Figure 12:
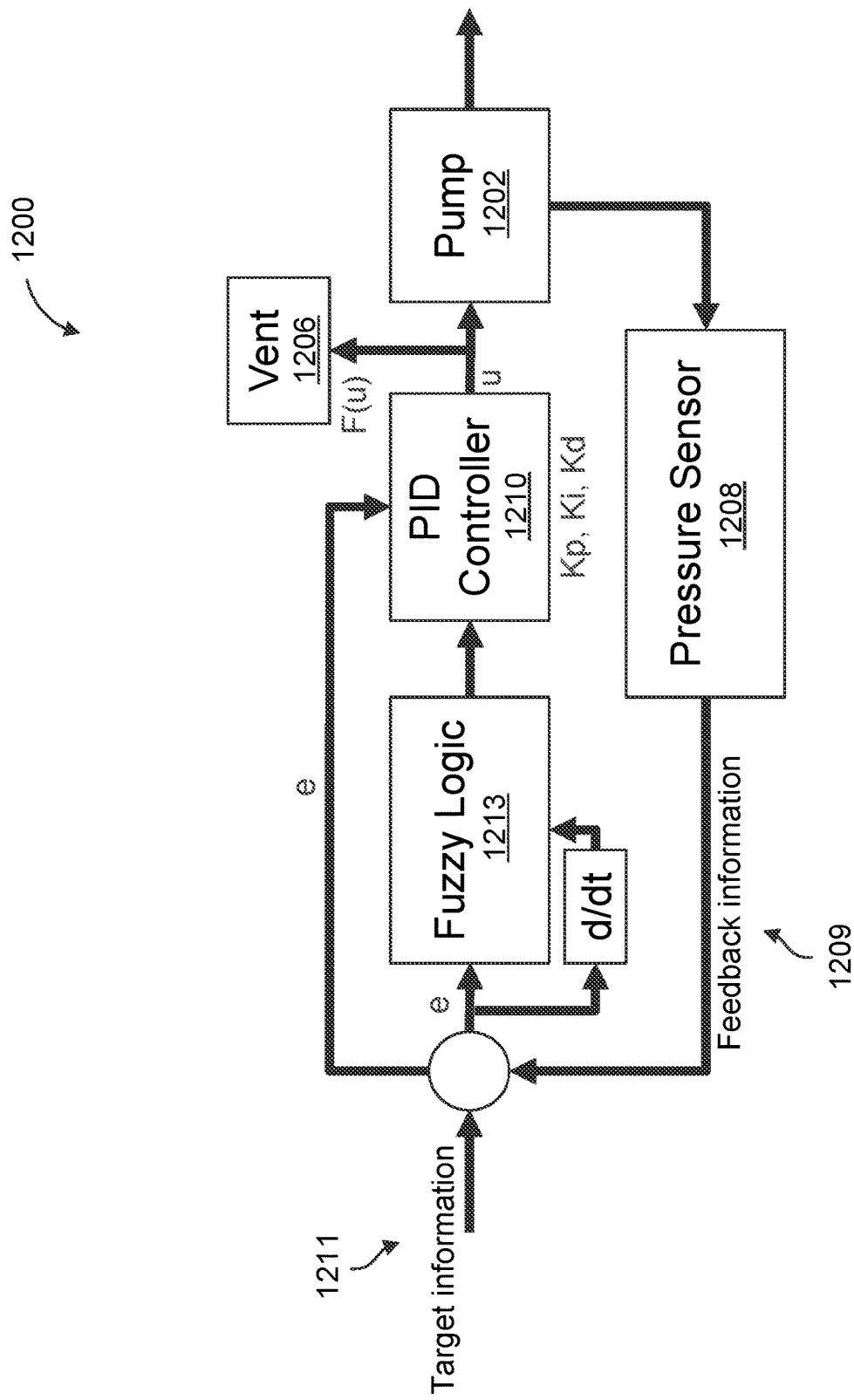
FIG. 12 is a block diagram of an example sensor apparatus using fuzzy logic and a PID controller according to some embodiments.

FIG. 12 is a block diagram of an example sensor apparatus 1200 using fuzzy logic 1213 and a PID controller 1210 according to some embodiments. The example sensor apparatus 1200 may further include a pump 1202, a vent 1206, and a pressure sensor 1208, which may be similar to or examples of their counterparts described with respect to FIGS. 10 and 11, and their descriptions will be omitted for brevity. In some embodiments, an input may be based on target information 1211 and feedback information 1209, e.g., a difference between a target pressure level and pressure of a bladder or airbag (not shown) measured by the pressure sensor 1208, or error e(t). The input may be fed to PID controller 1210 and/or fuzzy logic 1213. In some cases, the fuzzy logic 1213 itself may determine the error rather than being provided with it.

Figure 13:
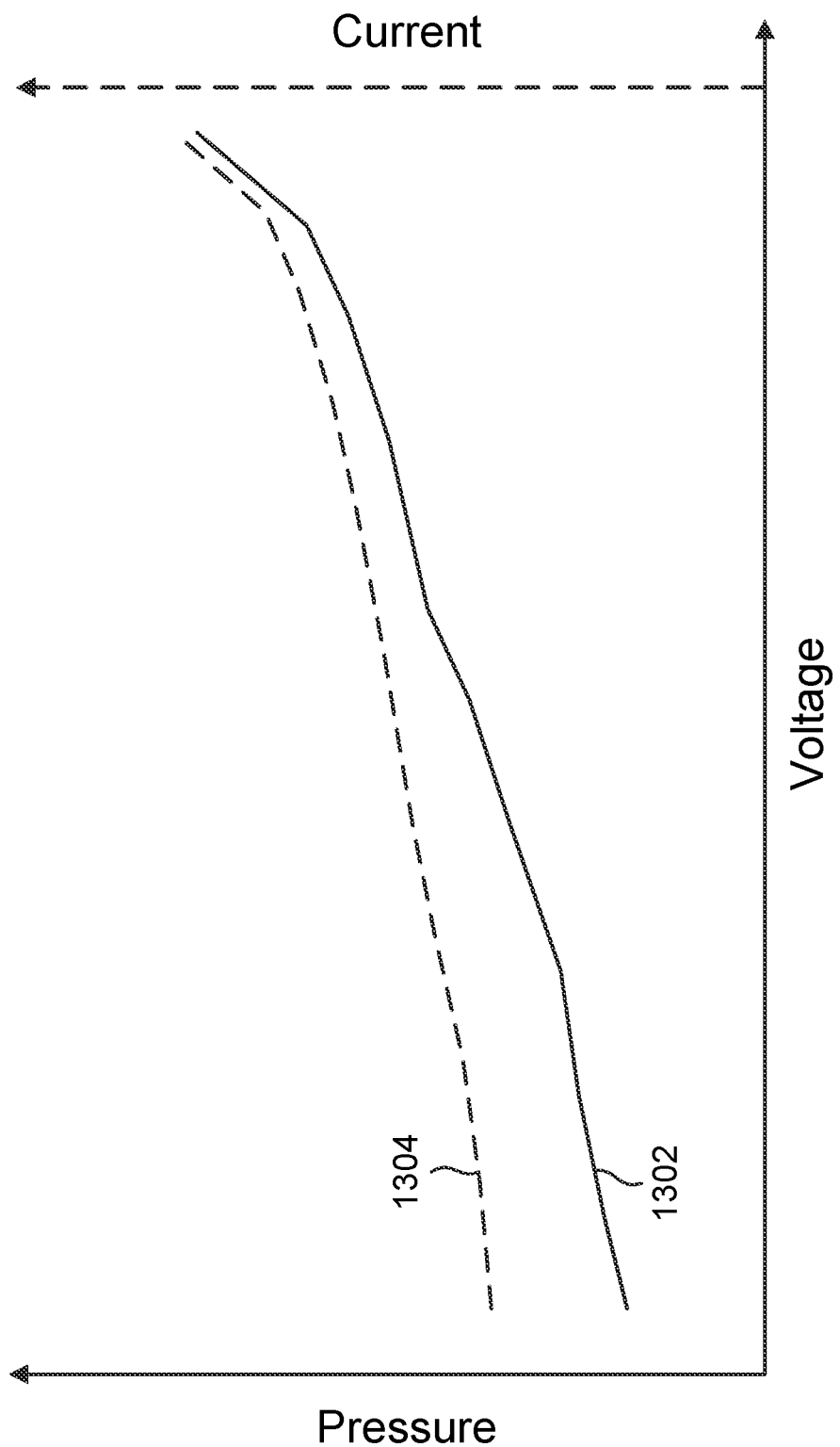
FIG. 13 shows graphs of pressure applied and current consumption as a function of voltage.

In some approaches, the fuzzy logic 1213 may determine through fuzzification and defuzzification processes described above that the pressure detected and indicated in the feedback information 1209 is too high, too low, or sufficient compared to the target pressure level indicated by the target information 1211. Information or a control signal corresponding to a voltage level configured to compensate for any deviation from the target pressure may be generated and output. The PID controller 1210 may use the error to determine Kp, Ki, Kd and generate an output including information or a control signal for the pump 1202 (e.g., a voltage corresponding to the desired or target pressure level) and/or the vent 1206 (e.g., a control signal to open or close the vent 1206). Briefly, FIG. 13 shows graphs of pressure applied and current consumption as a function of voltage. Graph 1302 represents pressure as a function of voltage. Graph 1304 represents current consumption as a function of voltage. As can be seen, there is a general proportional correlation between voltage and pressure and current. This information may be useful for determining the amount of voltage to apply for the desired pressure to be applied.

In some cases, the PID controller 1210 may compare the information that it output with the information output by the fuzzy logic 1213. If there is a substantial difference, e.g., a difference between the outputs that exceed an error threshold, one or both of the outputs may be discarded. If there is an acceptable difference, e.g., within the error threshold, the output of the PID controller 1210 or the output of the fuzzy logic 1213 may be used to control the pump 1202 and/or the vent 1206.

Thus, example sensor apparatus 1200 may use a closed-loop system to control and hold the pressure level. More specifically, a voltage or signal corresponding to the desired target pressure level may be applied to the pump 1202 and/or the vent 1206 as described herein. Based on the timing of the inflation or deflation, sensor measurements may be taken.

Example operations involving the example sensor apparatus 1100 or 1200 may include one or more of the following. (1) The airbag 1104 may be inflated by the pump 1202 based on applying an initial voltage to the pump driver 1112.

(2) The control system 1101 and/or the controller 1110 (which may implement or be implemented as a PID controller 1110, 1210) may keep track of differences between target voltage and feedback voltage, and generate a control signal indicative of voltage to the pump driver 1112. Fuzzy logic 1113, 1213 may also be used to evaluate the differences.

(3) The control system 1101 and/or the controller 1110 may control the vent 1106 using a control signal configured to close or open the vent 1106.

(4) The control system 1101 and/or the controller 1110 may turn off the pump 1102 when the PID error ($e(t)$) is smaller than a threshold, which may indicate that the pressure has reached the target pressure.

(5a) The sensor 1118 (e.g., a photoacoustic sensor) may make measurements with respect to a target object (e.g., a blood vessel of a user) while the pump 1202 is off. The pressure applied by the airbag 1104 to the user may be held at the target pressure.

(5b) Changes in condition(s) such as temperature or altitude may occur and cause the applied pressure to change accordingly. For example, the temperature may have dropped and reduced the pressure, or the temperature may have increased (e.g., at least partly due to higher temperature or prolonged operation of the sensor apparatus). In such scenarios, the pressure of the airbag 1104 may be compensated accordingly (e.g., apply a voltage to the pump driver 1112 to increase the pressure in the airbag 1104). Voltage used for compensation may be determined by the PID controller 1110, 1210 and/or the fuzzy logic 1113, 1213 as discussed above.

(6) The control system 1101 and/or the controller 1110 may inflate the airbag 1104 to the next target pressure. In some implementations, a new control signal indicative of a new pump voltage may be generated. In some cases, another new control signal configured to turn the vent 1106 on or off as appropriate may be generated. The new control signal(s) may be applied to the pump driver 1112 and/or the until the vent 1106 until the new target pressure is reached, thereby creating a staircase pressure profile such as that shown in FIG. 9 (without pressure compensations) or 9A (with pressure compensation(s)).

During any transition periods where the pressure is being changed, whether based on the next target pressure or a need for compensation, the photoacoustic sensor may not make measurements to mitigate noise interference caused by operation of the pump 1202 or the vent 1106 (or other components that create noise during operation).

Machine Learning

In some embodiments, a machine learning model may be used to predict a physiological parameter, e.g., blood pressure of the user. In some embodiments, a machine learning model may be used to predict a voltage (e.g., to apply to a pump) based on target pressure information and measured feedback pressure information. A machine learning model (or artificial intelligence model) may refer to a computational algorithm that indicates relationships between input variables and output variables. In some embodiments, a machine learning model can be trained. Training a machine learning model may involve, among other things, determining values of weights associated with the machine learning model, where relationships between the input variables and the output variables are based at least in part on the determined weight values. In one implementation, a machine learning model may be trained in a supervised manner using a training set that includes labeled training data. In a more particular example, the labeled training data may include inputs and manually annotated outputs that the machine learning model is to approximate using determined weight values. In another implementation, a machine learning model may be trained in an unsupervised manner in which weight values are determined without manually labeled training data.

An example training process for the machine learning model may involve providing training data that includes various data such as known target pressures, measured feedback pressures, current temperature, current altitude, change in temperature, change in altitude, known differences (errors) between target pressure and measured feedback pressure, time to inflate or deflate, and/or fuzzy variables, as well as labeled "ground truth" or the known output characteristics or parameters, e.g., voltage to apply to a pump (if the goal of the model is to determine the voltage) or blood pressure of a user (if the goal of the model is to predict the blood pressure). In some approaches, a portion (e.g., 20%) of the training data may be used as part of a validation set for the machine learning model. With this training data and validation set, one or more loss functions may be implemented. A loss function is an optimization function in which an error is iteratively minimized through, e.g., gradient descent. A productive learning rate that dictates the "step" the gradient descent takes when finding the lowest error may be set during training as well. One or more parameters of the machine learning model may be tuned and optimized during this learning process so that prediction outputs become more accurate.

As a result, a trained machine learning model can be generated. In some implementations, such a trained machine learning model can be used to further enhance the accuracy and reliability of the estimated physiological characteristics or parameter. For example, a blood pressure of the user derived based on sensor measurements can be provided to the machine learning model (stored at a sensor or a host device and/or accessible by a control system thereof) to compare with the blood pressure estimated by the machine learning model. If there is a discrepancy between the sensor-based estimation and the model-generated prediction which is greater than a threshold, the obtained estimation may be further evaluated or discarded. If discarded, the model-generated prediction may be used, or additional measurements may be taken by the sensors. On the other hand, if the discrepancy is lower than a threshold, the sensor-based estimation may be selected or kept for use.

PWV and Pressure Data

One salient use for the staircase pressure levels is that data representative of the discrete pressure levels can be provided as part of an input to a prediction model for estimating a physiological parameter (e.g., blood pressure) of a user. In some configurations, the predictive model may be a machine learning model. The pressure levels may be provided as input to the predictive model in the form of one or more graphs (e.g., graph 900 or 920), or in a data structure such as a list, matrix, table, etc. that includes pressure levels and/or other types of information such as duration, time, transition periods, errors, temperature changes, etc.

In some embodiments, a sensor (e.g., photoacoustic sensor) may obtain measurements during times where the pressure applied to a user is at a discrete pressure level (e.g., 906, 910, 914, 918, 924, 926), or a portion of those times when there are no corrective changes in pressure being made, e.g., transition periods 935, 937 associated with alternate pressure levels 925, 927.

Figure 14:
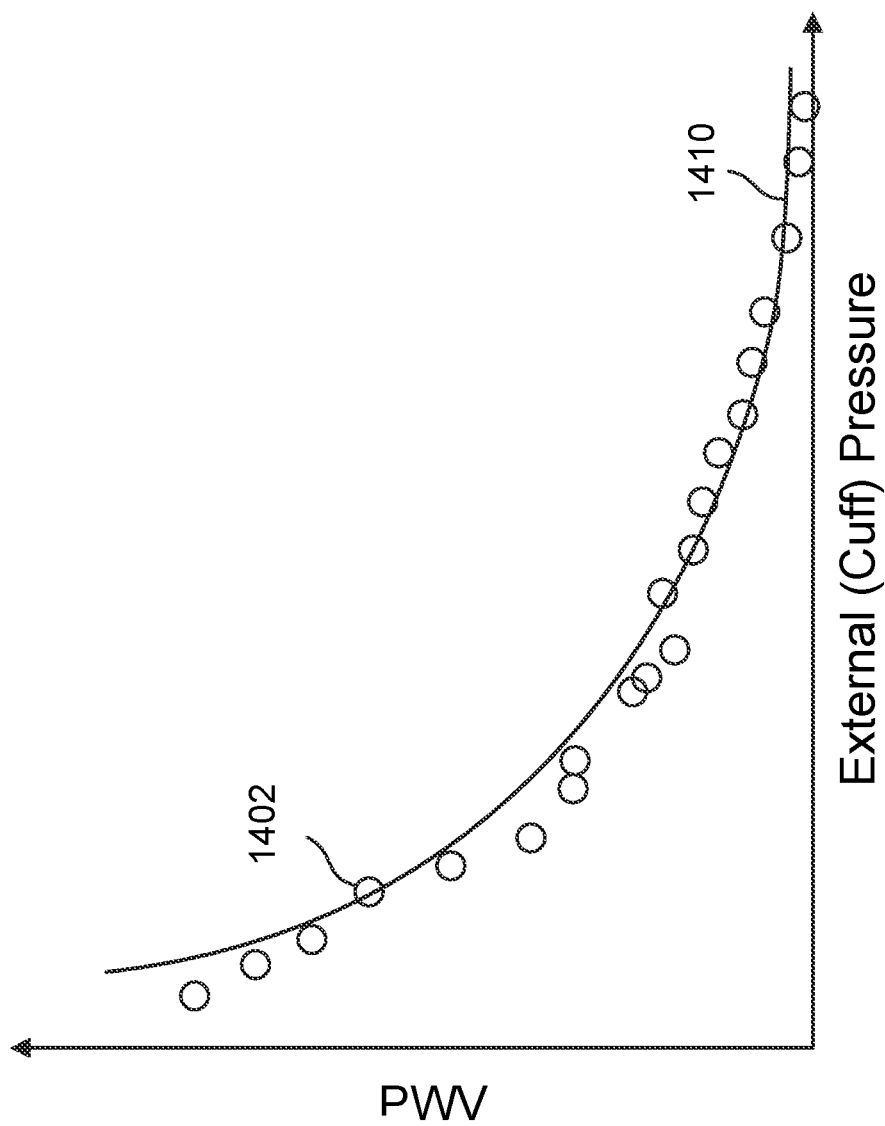
FIG. 14 is a graph of an example set of data points of pulse wave velocity (PWV) as a function of applied external pressure, according to some embodiments.

Hence, PWV data corresponding to respective ones of the pressure levels may be obtained using this approach. In some embodiments, a multiple-point PWV curve may be generated. FIG. 14 is a graph of an example set of data points 1402 of PWV as a function of applied external pressure, according to some embodiments. In some approaches, a curve 1410 may be fitted on the data points 1402, e.g., an exponential curve, a polynomial curve, or a logarithmic curve. In some cases, the curve 1410 may be linear depending on the range of data points or how limited the data is; a smaller segment of the curve 1410 may be substantially linear. In some cases, a slope of the curve 1410 may provide useful information, such as compliance or part of the Bramwell-Hill equation, which relates arterial distensibility, pressure variation, and PWV.

Some or all of the above information may be provided to the aforementioned prediction model for training and/or inference of the predictive model. In some approaches, training the predictive model may further include providing a set of labeled ground truth blood pressure data, e.g., known blood pressures in view of the PWV and pressure data.

In some embodiments, a control system or controller of the type described above may be configured to implement the predictive model. In some configurations, the predictive model may be trained to output the blood pressure of the user based on input data comprising a plurality of PWVs and a plurality of discrete pressure levels.

Example Methods

Figure 15:
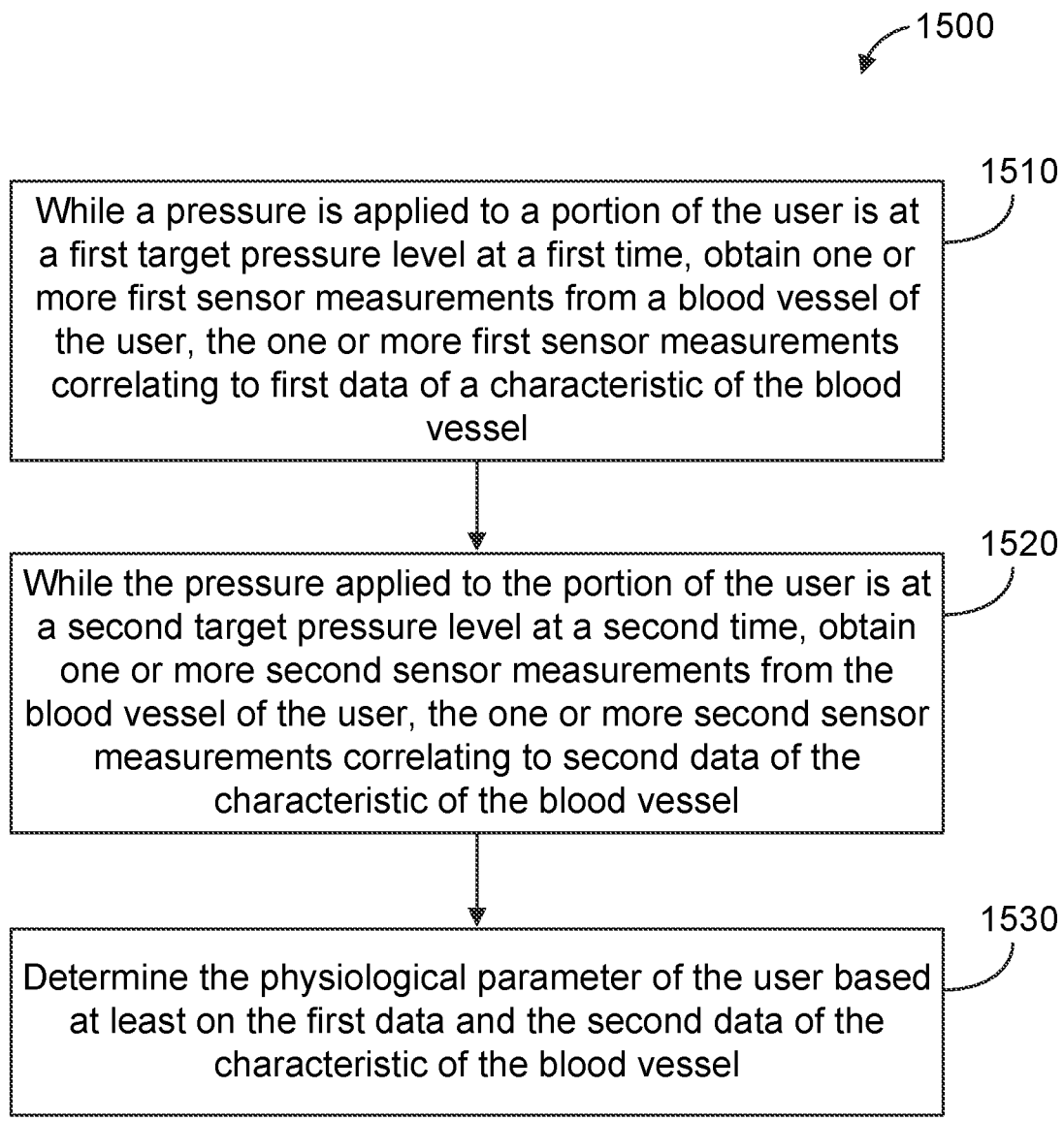
FIG. 15 is a flow diagram of a method for determining a physiological parameter of a user, according to some disclosed embodiments.

FIG. 15 is a flow diagram of a method 1500 for determining a physiological parameter of a user, according to some disclosed embodiments. Structure for performing the functionality illustrated in one or more of the blocks shown in FIG. 15 may be performed by hardware and/or software components of a computerized apparatus or system (which may be implemented as a wearable user device in some embodiments). Components of such apparatus or system may include, for example, one or more sensors, a control system (including one or more processors), a memory, and/or a computer-readable apparatus including a storage medium storing computer-readable and/or computer-executable instructions that are configured to, when executed by the control system, cause the control system, the one or more processors, or the apparatus to perform operations represented by blocks below. Example components of the apparatus are illustrated in FIGS. 2, 6, 7, 10, 11 and 12, which are described in more detail above.

The blocks of FIG. 15 may, for example, be performed by the apparatus shown in the above Figures or by a similar apparatus, or a component thereof (e.g., a control system). As with other methods disclosed herein, the method outlined in FIG. 15 may include more or fewer blocks than indicated. Moreover, the blocks of methods disclosed herein are not necessarily performed in the order indicated. In some instances, one or more of the blocks shown in FIG. 15 may be performed concurrently.

At block 1510, the method 1500 may include, while a pressure is applied to a portion of the user is at a first target pressure level at a first time, obtaining one or more first sensor measurements from a blood vessel of the user, the one or more first sensor measurements correlating to first data of a characteristic of the blood vessel. In some embodiments, the first data of the characteristic of the blood vessel may include a first pulse wave velocity (PWV) of the blood vessel.

Means for performing functionality at block 1510 may include, the interface 201, the receiver system 202, and the light source system 204, the cuff system 205, the biometric sensor 212 (sensor 622, 722, 1018, 1118), the pump 604, 714, 1002, 1102, 1202, the bladder 608, 740 (airbag 1004, 1104), vent 610, 1006, 1106, 1206, and/or other components of the apparatus as shown in FIGS. 2, 6, 7, 10, 11, and 12.

At block 1520, the method 1500 may include, while the pressure applied to the portion of the user is at a second target pressure level at a second time, obtaining one or more second sensor measurements from the blood vessel of the user, the one or more second sensor measurements correlating to second data of the characteristic of the blood vessel. In some embodiments, the second data of the characteristic of the blood vessel may include a second PWV of the blood vessel.

In some embodiments, the pressure applied to the portion of the user at the first target pressure level and the second target pressure level may be based on a calibrated relationship between the first and second target pressure levels and corresponding voltage levels applicable to the wearable user device.

Means for performing functionality at block 1520 may include, the interface 201, the receiver system 202, and the light source system 204, the cuff system 205, the biometric sensor 212 (sensor 622, 722, 1018, 1118), the pump 604, 714, 1002, 1102, 1202, the bladder 608, 740 (airbag 1004, 1104), vent 610, 1006, 1106, 1206, and/or other components of the apparatus as shown in FIGS. 2, 6, 7, 10, 11, and 12.

At block 1530, the method 1500 may include, determining the physiological parameter of the user based at least on the first data and the second data of the characteristic of the blood vessel. In some embodiments, the wearable user device may further include a control system configured to implement a predictive model configured to output the physiological parameter (e.g., a blood pressure) of the user based on input data comprising a plurality of PWVs (e.g., the first PWV and the second PWV of the blood vessel) and a plurality of discrete pressure levels (e.g., the first target pressure level and the second target pressure level). In some cases, PWV obtained during discrete pressure levels can be used to determine blood pressure using relationships, such as the Bramwell-Hill equation. However, the approaches described herein provide a salient advantage in that the biometric measurements (e.g., photoacoustic measurements) and thus PWVs obtained using the embodiments described herein are clean data that is less prone to noise and errors than prior approaches.

Means for performing functionality at block 1530 may include the control system 206, the controller 602, the main board 712, the control board 718, the controller 1010, the control system 1101, controller 1110, and/or other components of the apparatus as shown in FIGS. 2, 6, 7, 10, 11, and 12.

In some embodiments, the wearable user device or a cuff of the wearable user device may be configured to stop operation while the applied pressure is at one of a plurality of discrete pressure levels (e.g., the first target pressure level, the second target pressure level), and to operate to apply the pressure during one or more transitions between the two of the plurality of discrete pressure levels; and a biometric sensor of the wearable user device may be configured to obtain the sensor measurements while the applied pressure is at the plurality of discrete pressure levels, and not obtain the sensor measurements during the one or more transitions between the plurality of discrete pressure levels. In some implementations, a biometric sensor may obtain the sensor measurements, wherein the biometric sensor may include a photoacoustic sensor may be configured to obtain photoacoustic signals generated from light incident on a blood vessel of the user, an acoustic sensor configured to obtain acoustic signals, or both. In some implementations, the cuff may be further configured to, responsive to the pressure applied to the portion of the user deviating from the plurality of discrete pressure levels, adjust the pressure to one of the plurality of discrete pressure levels based on a calibrated relationship between the plurality of discrete pressure levels and corresponding voltage levels.

In some embodiments, the method 1500 may further include, while a vent of the wearable user device is closed: setting the pressure applied to the portion of the user to the first target pressure level by applying, to an inflatable portion of the wearable user device, a first voltage corresponding to the first target pressure level; and subsequent to the first target pressure level being reached, lowering the first voltage applied to the inflatable portion to zero. The one or more first sensor measurements from the blood vessel of the user may be obtained while the first voltage applied to the inflatable portion is at zero. In some implementations, the method 1500 may further include, subsequent to the obtaining of the one or more first sensor measurements: while the vent of the wearable user device is closed: setting the pressure applied to the portion of the user to the second target pressure level by applying, to the inflatable portion of the wearable user device, a second voltage corresponding to the second target pressure level; and subsequent to the second target pressure level being reached, lowering the second voltage applied to the inflatable portion to zero. The one or more second sensor measurements from the blood vessel of the user may be obtained while the second voltage applied to the inflatable portion is at zero.

In some embodiments, the method 1500 may further include increasing or decreasing the pressure applied to the portion of the user during a transition period between the first time and the second time via operation of a cuff of the wearable user device. In some approaches, the method 1500 may further include preventing sensor measurements during operation of the cuff. In some approaches, the obtaining of the one or more first sensor measurements and the one or more second sensor measurements may occur while the cuff is not operational.

In some embodiments, the method 1500 may further include detecting that the pressure applied to the portion of the user has deviated from the first target pressure level or the second target pressure level; and responsive to the deviation of the pressure, adjusting the pressure applied to the portion of the user to the first target pressure level or the second target pressure level.

In some embodiments, the method 1500 may further include determining a current pressure applied to the portion of the user; wherein the pressure applied to the portion of the user at the first target pressure level and the second target pressure level is based at least on a feedback loop involving a difference between the current pressure and a target pressure level. In some implementations, the method 1500 may further include determining a voltage level to compensate for the difference between the current pressure and a target pressure level. In some implementations, the voltage level may be determined by fuzzy logic, a neural network, a proportional-integral-derivative (PID) controller, or a combination thereof.

Figure 16:
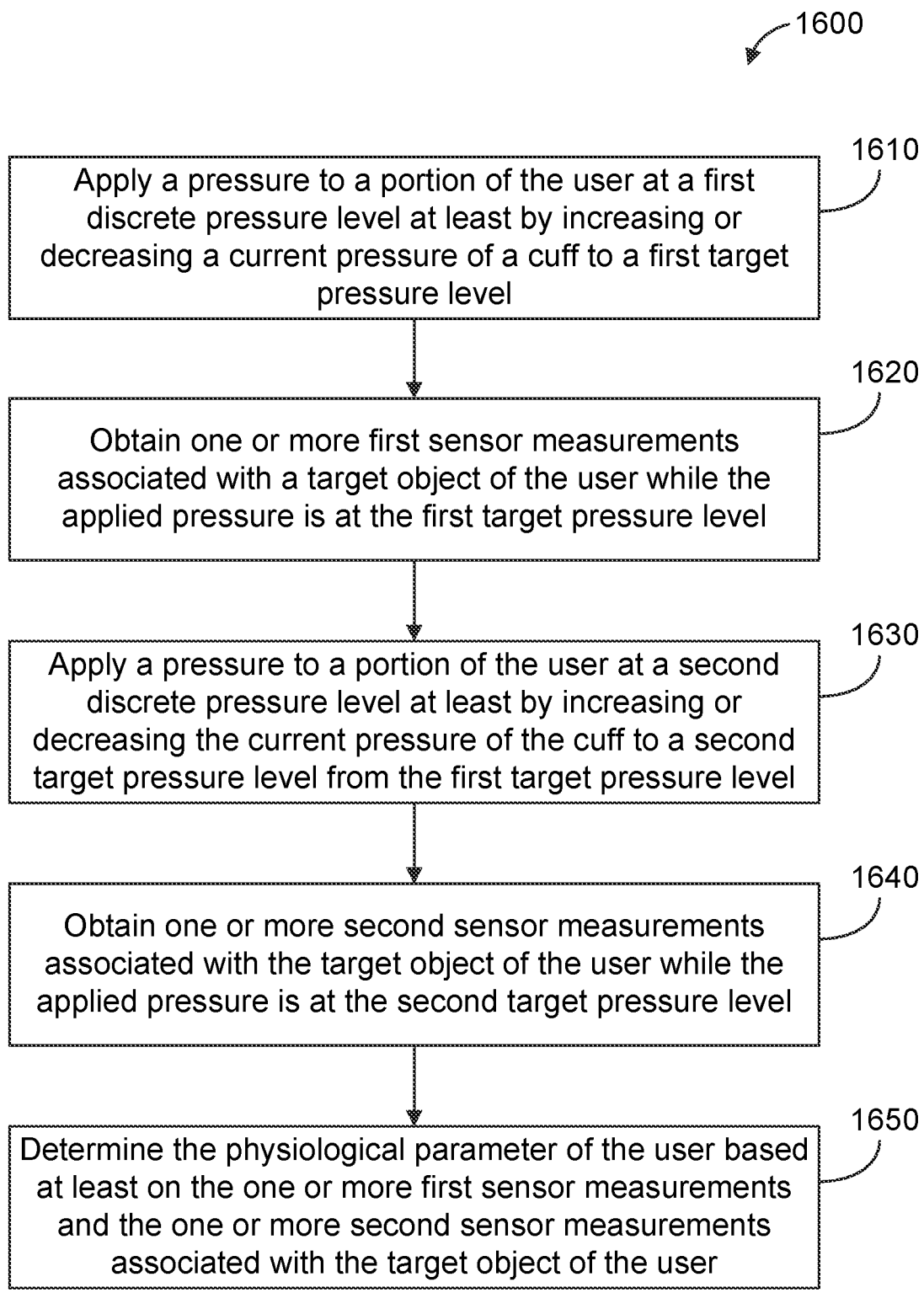
FIG. 16 is a flow diagram of another method for determining a physiological parameter of a user, according to some disclosed embodiments.

FIG. 16 is a flow diagram of a method 1600 for determining a physiological parameter of a user, according to some disclosed embodiments. Structure for performing the functionality illustrated in one or more of the blocks shown in FIG. 16 may be performed by hardware and/or software components of a computerized apparatus or system (which may be implemented as a wearable device in some embodiments). Components of such apparatus or system may include, for example, one or more sensors, a control system (including one or more processors), a memory, and/or a computer-readable apparatus including a storage medium storing computer-readable and/or computer-executable instructions that are configured to, when executed by the control system, cause the control system, the one or more processors, or the apparatus to perform operations represented by blocks below. Example components of the apparatus are illustrated in FIGS. 2, 6, 7, 10, 11 and 12, which are described in more detail above.

The blocks of FIG. 16 may, for example, be performed by the apparatus shown in the above Figures or by a similar apparatus, or a component thereof (e.g., a control system). As with other methods disclosed herein, the method outlined in FIG. 16 may include more or fewer blocks than indicated. Moreover, the blocks of methods disclosed herein are not necessarily performed in the order indicated. In some instances, one or more of the blocks shown in FIG. 16 may be performed concurrently.

At block 1610, the method 1600 may include applying a pressure to a portion of the user at a first discrete pressure level at least by increasing or decreasing a current pressure of a cuff to a first target pressure level.

In some implementations, increasing the current pressure of the cuff to the first target pressure level may include inflating a portion (e.g., a bladder, an airbag) the cuff based on a corresponding voltage applied to a pump associated with the cuff. In some configurations, a vent associated with the cuff may be closed while the current pressure of the cuff is being increased. In some implementations, decreasing the current pressure of the cuff to the first target pressure level may include deflating a portion of the cuff, inflating a portion of the cuff, or a combination thereof. In some configurations, deflating the portion of the cuff may include opening a vent associated with the cuff. In some configurations, decreasing the current pressure of the cuff to the first target pressure level may include deflating the portion of the cuff below the first target pressure level, and then subsequently inflating the portion of the cuff based on a corresponding voltage applied to the pump.

Means for performing functionality at block 1610 may include the cuff system 205, the pump 604, 714, 1002, 1102, 1202, the bladder 608, 740 (airbag 1004, 1104), vent 610, 1006, 1106, 1206, and/or other components of the apparatus as shown in FIGS. 2, 6, 7, 10, 11, and 12.

At block 1620, the method 1600 may include obtaining one or more first sensor measurements associated with a target object of the user while the applied pressure is at the first target pressure level. In some embodiments, obtaining the one or more first sensor measurements associated with the target object of the user may include using a photoacoustic sensor to obtain one or more photoacoustic measurements generated from light incident on a blood vessel of the user. In some embodiments, the one or more first sensor measurements are not obtained while the applied pressure is not at the first target pressure level (or any target pressure level), e.g., during transition periods between target pressure levels.

Means for performing functionality at block 1620 may include the interface 201, the receiver system 202, and the light source system 204, the cuff system 205, the biometric sensor 212 (sensor 622, 722, 1018, 1118), the bladder 608, 740 (airbag 1004, 1104), vent 610, 1006, 1106, 1206, and/or other components of the apparatus as shown in FIGS. 2, 6, 7, 10, 11, and 12.

At block 1630, the method 1600 may include applying a pressure to a portion of the user at a second discrete pressure level at least by increasing or decreasing the current pressure of the cuff to a second target pressure level from the first target pressure level. Increasing or decreasing the current pressure may be similar to the operations described with respect to block 1610.

Means for performing functionality at block 1630 may include the cuff system 205, the pump 604, 714, 1002, 1102, 1202, the bladder 608, 740 (airbag 1004, 1104), vent 610, 1006, 1106, 1206, and/or other components of the apparatus as shown in FIGS. 2, 6, 7, 10, 11, and 12.

At block 1640, the method 1600 may include obtaining one or more second sensor measurements associated with the target object of the user while the applied pressure is at the second target pressure level. Obtaining the one or more second sensor measurements while the applied pressure is at the second target pressure level may be similar to the operations described with respect to block 1620.

Means for performing functionality at block 1640 may include the interface 201, the receiver system 202, and the light source system 204, the cuff system 205, the biometric sensor 212 (sensor 622, 722, 1018, 1118), the bladder 608, 740 (airbag 1004, 1104), vent 610, 1006, 1106, 1206, and/or other components of the apparatus as shown in FIGS. 2, 6, 7, 10, 11, and 12.

At block 1650, the method 1600 may include determining the physiological parameter of the user based at least on the one or more first sensor measurements and the one or more second sensor measurements associated with the target object of the user. In some embodiments, the physiological parameter of the user may include a blood pressure of the user. In some embodiments, a plurality of PWVs of a blood vessel of the user may be derived from the one or more first sensor measurements and the one or more second sensor measurements. In some embodiments, a predictive model (e.g., a machine learning model) may be configured to determine the blood pressure of the user using an approach described above, including using data associated with the plurality of PWVs of the blood vessel and the first and second target pressure levels.

A feedback loop may be implemented to keep the discrete pressure levels according to target pressure levels. In some scenarios, the current pressure of the cuff, the first target pressure level, or the second target pressure level may deviate from the intended pressure levels, as a result of, e.g., temperature fluctuations, operation time, and/or altitude changes. In some embodiments, feedback information from a pressure sensor (e.g., pressure at the cuff or voltage at the pump) and target information (e.g., target pressure or target voltage for the cuff), may be used to correct the pressure applied to the portion of the user. In some implementations thereof, a PID controller may determine an optimized voltage level to be applied to the pump of the cuff to increase the current pressure to the correct pressure level, or a control signal to the vent of the cuff to decrease the current pressure to the correct pressure level. In some implementations, fuzzy logic may be used to determine the voltage level for the pump or control signal for the vent. In some implementations, a neural network may be used to determine the voltage level for the pump or control signal for the vent.

Means for performing functionality at block 1650 may include the control system 206, the controller 602, the main board 712, the control board 718, the controller 1010, the control system 1101, controller 1110, and/or other components of the apparatus as shown in FIGS. 2, 6, 7, 10, 11, and 12.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

Implementation examples are described in the following numbered clauses:

Clause 1: A wearable user device comprising: a cuff configured to apply a pressure to a portion of a user at a plurality of discrete pressure levels over a plurality of time periods; a biometric sensor configured to obtain a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user; and a wearable structure comprising the cuff and the biometric sensor.

Clause 2: The wearable user device of clause 1, wherein: the cuff is further configured to stop operation while the applied pressure is at one of the plurality of discrete pressure levels, and to operate to apply the pressure during one or more transitions between the two of the plurality of discrete pressure levels; and the biometric sensor is further configured to obtain the plurality of sensor measurements while the applied pressure is at the plurality of discrete pressure levels, and not obtain the plurality of sensor measurements during the one or more transitions between the plurality of discrete pressure levels.

Clause 3: The wearable user device of any one of clauses 1-2 wherein the characteristic of the blood vessel comprises a pulse wave velocity (PWV) of the blood vessel; the plurality of data of the characteristic of the blood vessel comprises a plurality of PWVs corresponding to respective ones of the plurality of discrete pressure levels; and the blood pressure of the user is determined based on the plurality of PWVs and the plurality of discrete pressure levels.

Clause 4: The wearable user device of any one of clauses 1-3 further comprising a control system configured to implement a predictive model configured to output the blood pressure of the user based on input data comprising the plurality of PWVs and the plurality of discrete pressure levels.

Clause 5: The wearable user device of any one of clauses 1-4 wherein the biometric sensor comprises a photoacoustic sensor configured to obtain photoacoustic signals generated from light incident on a blood vessel of the user, an acoustic sensor configured to obtain acoustic signals, or both.

Clause 6: The wearable user device of any one of clauses 1-5 wherein the cuff further comprises: an air bladder configured to maintain the pressure to the portion of the user at each of the plurality of discrete pressure levels according to corresponding voltage levels; and a vent configured to be closed during inflation of the air bladder and the maintenance of the pressure, and open during deflation of the air bladder.

Clause 7: The wearable user device of any one of clauses 1-6 further comprising a pressure sensor configured to detect that the pressure applied to the portion of the user has deviated from the plurality of discrete pressure levels; wherein, responsive to the deviation of the pressure, the cuff is further configured to adjust the pressure to one of the plurality of discrete pressure levels.

Clause 8: The wearable user device of any one of clauses 1-7 wherein the pressure applied to the portion of the user at the plurality of discrete pressure levels is based on a calibrated relationship between the plurality of discrete pressure levels and corresponding voltage levels applicable to the cuff.

Clause 9: The wearable user device of any one of clauses 1-8 wherein the cuff is further configured to, responsive to the pressure applied to the portion of the user deviating from the plurality of discrete pressure levels, adjust the pressure to one of the plurality of discrete pressure levels based on the calibrated relationship between the plurality of discrete pressure levels and the corresponding voltage levels.

Clause 10: The wearable user device of any one of clauses 1-9 further comprising a pressure sensor configured to determine a current pressure applied to the portion of the user, and a voltage level corresponding to the current pressure; wherein the pressure applied to the portion of the user at the plurality of discrete pressure levels is based at least on a feedback loop of minimizing a difference between (i) the voltage corresponding to the current pressure provided by the pressure sensor and (ii) a target voltage.

Clause 11: The wearable user device of any one of clauses 1-10 wherein a voltage level corresponding to the pressure applied to the portion of the user is generated at least partly using a neural network receiving the current pressure, the voltage level corresponding to the current pressure, a current temperature associated with the cuff, the target voltage, or a combination thereof.

Clause 12: The wearable user device of any one of clauses 1-11 further comprising a control system, the control system configured to implement fuzzy logic via the neural network to generate the voltage level corresponding to the pressure applied to the portion of the user.

Clause 13: The wearable user device of any one of clauses 1-12 wherein the plurality of data of the characteristic of the blood vessel comprises a plurality of PWVs corresponding to respective ones of the plurality of discrete pressure levels; and the wearable user device further comprising a control system, the control system configured to determine the blood pressure of the user based on the plurality of PWVs.

Clause 14: The wearable user device of any one of clauses 1-13 wherein the control system is further configured to determine the blood pressure of the user based on a prediction model, the prediction model configured to receive as input a curve of the plurality of PWVs as a function of the plurality of discrete pressure levels.

Clause 15: The wearable user device of any one of clauses 1-14 wherein the plurality of discrete pressure levels comprise a range of pressure levels between 20 and 90 mmHg inclusive.

Clause 16: A method of determining a physiological parameter of a user using a wearable user device, the method comprising: while a pressure is applied to a portion of the user is at a first target pressure level at a first time, obtaining one or more first sensor measurements from a blood vessel of the user, the one or more first sensor measurements correlating to first data of a characteristic of the blood vessel; while the pressure applied to the portion of the user is at a second target pressure level at a second time, obtaining one or more second sensor measurements from the blood vessel of the user, the one or more second sensor measurements correlating to second data of the characteristic of the blood vessel; and determining the physiological parameter of the user based at least on the first data and the second data of the characteristic of the blood vessel.

Clause 17: The method of clause 16, further comprising: while a vent of the wearable user device is closed: setting the pressure applied to the portion of the user to the first target pressure level by applying, to an inflatable portion of the wearable user device, a first voltage corresponding to the first target pressure level; and subsequent to the first target pressure level being reached, lowering the first voltage applied to the inflatable portion to zero; wherein the one or more first sensor measurements from the blood vessel of the user are obtained while the first voltage applied to the inflatable portion is at zero.

Clause 18: The method of any one of clauses 16-17 further comprising, subsequent to the obtaining of the one or more first sensor measurements while the vent of the wearable user device is closed: setting the pressure applied to the portion of the user to the second target pressure level by applying, to the inflatable portion of the wearable user device, a second voltage corresponding to the second target pressure level; and subsequent to the second target pressure level being reached, lowering the second voltage applied to the inflatable portion to zero; wherein the one or more second sensor measurements from the blood vessel of the user are obtained while the second voltage applied to the inflatable portion is at zero.

Clause 19: The method of any one of clauses 16-18 further comprising increasing or decreasing the pressure applied to the portion of the user during a transition period between the first time and the second time via operation of a cuff of the wearable user device.

Clause 20: The method of any one of clauses 16-19 further comprising preventing sensor measurements during operation of the cuff.

Clause 21: The method of any one of clauses 16-20 wherein the obtaining of the one or more first sensor measurements and the one or more second sensor measurements occur while the cuff is not operational.

Clause 22: The method of any one of clauses 16-21 further comprising detecting that the pressure applied to the portion of the user has deviated from the first target pressure level or the second target pressure level; and responsive to the deviation of the pressure, adjusting the pressure applied to the portion of the user to the first target pressure level or the second target pressure level.

Clause 23: The method of any one of clauses 16-22 wherein the first data of the characteristic of the blood vessel comprises a first pulse wave velocity (PWV) of the blood vessel, and the second data of the characteristic of the blood vessel comprises a second PWV of the blood vessel.

Clause 24: The method of any one of clauses 16-23 wherein the pressure applied to the portion of the user at the first target pressure level and the second target pressure level is based on a calibrated relationship between the first and second target pressure levels and corresponding voltage levels applicable to the wearable user device.

Clause 25: The method of any one of clauses 16-24 further comprising determining a current pressure applied to the portion of the user; wherein the pressure applied to the portion of the user at the first target pressure level and the second target pressure level is based at least on a feedback loop involving a difference between (i) the current pressure and (ii) a target pressure level.

Clause 26: The method of any one of clauses 16-25 further comprising determining a voltage level to compensate for the difference between the current pressure and a target pressure level.

Clause 27: The method of any one of clauses 16-26 wherein the voltage level is determined by fuzzy logic, a neural network, a proportional-integral-derivative (PID) controller, or a combination thereof.

Clause 28: An apparatus comprising: means for applying a pressure to a portion of a user at a plurality of discrete pressure levels over a plurality of time periods; means for obtaining a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user; and wearable means comprising the means for applying the pressure to the portion of the user, and the means for obtaining the plurality of sensor measurements.

Clause 29: The apparatus of clause 28, wherein: the means for applying the pressure to the portion of the user comprises means for stopping operation while the applied pressure is at one of the plurality of discrete pressure levels, and means for operating to apply the pressure during one or more transitions between the two of the plurality of discrete pressure levels; and the means for obtaining the plurality of sensor measurements comprises means for obtaining the plurality of sensor measurements while the applied pressure is at the plurality of discrete pressure levels, and not obtaining the plurality of sensor measurements during the one or more transitions between the plurality of discrete pressure levels.

Clause 30: A non-transitory computer-readable apparatus comprising a storage medium, the storage medium comprising a plurality of instructions configured to, when executed by one or more processors, cause an apparatus to: while a pressure is applied to a portion of a user is at a first target pressure level at a first time, obtain one or more first sensor measurements from a blood vessel of the user, the one or more first sensor measurements correlating to first data of a characteristic of the blood vessel; while the pressure applied to the portion of the user is at a second target pressure level at a second time, obtain one or more second sensor measurements from the blood vessel of the user, the one or more second sensor measurements correlating to second data of the characteristic of the blood vessel; and determine a physiological parameter of the user based at least on the first data and the second data of the characteristic of the blood vessel.

What is claimed:

1. A wearable user device comprising:
   a cuff configured to apply a pressure to a portion of a user at a plurality of discrete pressure levels over a plurality of time periods;
   a biometric sensor configured to obtain a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user, wherein:
      the characteristic of the blood vessel comprises a pulse wave velocity (PWV) of the blood vessel; and
      the plurality of data of the characteristic of the blood vessel comprises a plurality of PWVs corresponding to respective ones of the plurality of discrete pressure levels;
   a wearable structure comprising the cuff and the biometric sensor; and
   a control system configured to implement a predictive model configured to determine the blood pressure of the user based on input data comprising the plurality of PWVs and the plurality of discrete pressure levels and to output the blood pressure of the user.

2. The wearable user device of claim 1, wherein the cuff includes a bladder, further comprising a pump configured to flow air into or out of the bladder, wherein:
   the pump is configured to stop operation while the applied pressure is at one of the plurality of discrete pressure levels;
   the cuff is configured to operate to apply the pressure during one or more transitions between two of the plurality of discrete pressure levels; and
   the biometric sensor is further configured to obtain the plurality of sensor measurements while the applied pressure is at the plurality of discrete pressure levels, and not obtain the plurality of sensor measurements during the one or more transitions between the plurality of discrete pressure levels.

3. The wearable user device of claim 1, wherein the biometric sensor comprises a photoacoustic sensor configured to obtain photoacoustic signals generated from light incident on the blood vessel of the user, an acoustic sensor configured to obtain acoustic signals, or both.

4. The wearable user device of claim 1, wherein the cuff further comprises:
an air bladder configured to maintain the pressure to the portion of the user at each of the plurality of discrete pressure levels according to corresponding voltage levels; and
a vent configured to be closed during inflation of the air bladder and the maintenance of the pressure, and open during deflation of the air bladder.

5. The wearable user device of claim 1, further comprising a pressure sensor configured to detect that the pressure applied to the portion of the user has deviated from the plurality of discrete pressure levels;
wherein, responsive to the deviation of the pressure, the cuff is further configured to adjust the pressure to one of the plurality of discrete pressure levels.

6. The wearable user device of claim 1, wherein the pressure applied to the portion of the user at the plurality of discrete pressure levels is based on a calibrated relationship between the plurality of discrete pressure levels and corresponding voltage levels applicable to the cuff.

7. The wearable user device of claim 6, wherein the cuff is further configured to, responsive to the pressure applied to the portion of the user deviating from the plurality of discrete pressure levels, adjust the pressure to one of the plurality of discrete pressure levels based on the calibrated relationship between the plurality of discrete pressure levels and the corresponding voltage levels.

8. The wearable user device of claim 1, further comprising a pressure sensor configured to determine a current pressure applied to the portion of the user, and a voltage level corresponding to the current pressure;
wherein the pressure applied to the portion of the user at the plurality of discrete pressure levels is based at least on a feedback loop of minimizing a difference between (i) the voltage level corresponding to the current pressure provided by the pressure sensor and (ii) a target voltage.

9. The wearable user device of claim 8, wherein a voltage level corresponding to the pressure applied to the portion of the user is determined using a neural network.

10. The wearable user device of claim 9, further comprising a control system, the control system configured to implement fuzzy logic via the neural network to generate the voltage level corresponding to the pressure applied to the portion of the user.

11. The wearable user device of claim 1, wherein the predictive model is configured to receive as input a curve of the plurality of PWVs as a function of the plurality of discrete pressure levels.

12. The wearable user device of claim 1, wherein the plurality of discrete pressure levels comprise a range of pressure levels between 20 and 90 mmHg inclusive.

13. A method of determining a physiological parameter of a user using a wearable user device, the method comprising:
while a pressure is applied to a portion of the user is at a first target pressure level at a first time, obtaining one or more first sensor measurements from a blood vessel of the user, the one or more first sensor measurements correlating to first data of a characteristic of the blood vessel, the characteristic of the blood vessel comprising a pulse wave velocity (PWV) of the blood vessel and the first data comprising one or more PWV measurements at the first target pressure level;
while the pressure applied to the portion of the user is at a second target pressure level at a second time, obtaining one or more second sensor measurements from the blood vessel of the user, the one or more second sensor measurements correlating to second data of the characteristic of the blood vessel, the second data comprising one or more PWV measurements at the second target pressure level; and
determining the physiological parameter of the user by implementing a predictive model based at least on the first data and the second data of the characteristic of the blood vessel, wherein the physiological parameter comprises blood pressure.

14. The method of claim 13, further comprising:
while a vent of the wearable user device is closed:
setting the pressure applied to the portion of the user to the first target pressure level by applying, to an inflatable portion of the wearable user device, a first voltage corresponding to the first target pressure level; and
subsequent to the first target pressure level being reached, lowering the first voltage applied to the inflatable portion to zero;
wherein the one or more first sensor measurements from the blood vessel of the user are obtained while the first voltage applied to the inflatable portion is at zero.

15. The method of claim 14, further comprising, subsequent to the obtaining of the one or more first sensor measurements:
while the vent of the wearable user device is closed:
setting the pressure applied to the portion of the user to the second target pressure level by applying, to the inflatable portion of the wearable user device, a second voltage corresponding to the second target pressure level; and
subsequent to the second target pressure level being reached, lowering the second voltage applied to the inflatable portion to zero;
wherein the one or more second sensor measurements from the blood vessel of the user are obtained while the second voltage applied to the inflatable portion is at zero.

16. The method of claim 13, further comprising increasing or decreasing the pressure applied to the portion of the user during a transition period between the first time and the second time via operation of a cuff of the wearable user device.

17. The method of claim 16, further comprising preventing sensor measurements during operation of the cuff.

18. The method of claim 16, wherein the obtaining of the one or more first sensor measurements and the one or more second sensor measurements occur while the cuff is not operational.

19. The method of claim 13, further comprising:
detecting that the pressure applied to the portion of the user has deviated from the first target pressure level or the second target pressure level; and
responsive to the deviation of the pressure, adjusting the pressure applied to the portion of the user to the first target pressure level or the second target pressure level.

20. The method of claim 13, wherein the pressure applied to the portion of the user at the first target pressure level and the second target pressure level is based on a calibrated relationship between the first and second target pressure levels and corresponding voltage levels applicable to the wearable user device.

21. The method of claim 13, further comprising determining a current pressure applied to the portion of the user; wherein the pressure applied to the portion of the user at the first target pressure level and the second target pressure level is based at least on a feedback loop involving a difference between (i) the current pressure and (ii) a target pressure level.

22. The method of claim 21, further comprising determining a voltage level to compensate for the difference between the current pressure and the target pressure level.

23. The method of claim 22, wherein the voltage level is determined by fuzzy logic, a neural network, a proportional-integral-derivative (PID) controller, or a combination thereof.

24. An apparatus comprising:
   means for applying a pressure to a portion of a user at a plurality of discrete pressure levels over a plurality of time periods;
   means for obtaining a plurality of sensor measurements associated with a blood vessel of the user at corresponding ones of the plurality of discrete pressure levels during corresponding ones of the plurality of time periods, the plurality of sensor measurements correlating to a plurality of data of a characteristic of the blood vessel of the user, the plurality of data of the characteristic of the blood vessel enabling determination of a blood pressure of the user, wherein:
      the characteristic of the blood vessel comprises a pulse wave velocity (PWV) of the blood vessel; and
      the plurality of data of the characteristic of the blood vessel comprises a plurality of PWVs corresponding to respective ones of the plurality of discrete pressure levels;
   wearable means comprising the means for applying the pressure to the portion of the user, and the means for obtaining the plurality of sensor measurements; and
   control means for implementing a predictive model configured to determine the blood pressure of the user based on input data comprising the plurality of PWVs and the plurality of discrete pressure levels and to output the blood pressure of the user.

25. The apparatus of claim 24, wherein:
   the means for applying the pressure to the portion of the user comprises means for stopping operation while the applied pressure is at one of the plurality of discrete pressure levels, and means for operating to apply the pressure during one or more transitions between the two of the plurality of discrete pressure levels; and
   the means for obtaining the plurality of sensor measurements comprises means for obtaining the plurality of sensor measurements while the applied pressure is at the plurality of discrete pressure levels, and not obtaining the plurality of sensor measurements during the one or more transitions between the plurality of discrete pressure levels.

26. A non-transitory computer-readable apparatus comprising a storage medium, the storage medium comprising a plurality of instructions configured to, when executed by one or more processors, cause an apparatus to:
   while a pressure is applied to a portion of the user is at a first target pressure level at a first time, obtaining one or more first sensor measurements from a blood vessel of the user, the one or more first sensor measurements correlating to first data of a characteristic of the blood vessel, the characteristic of the blood vessel comprising a pulse wave velocity (PWV) of the blood vessel and the first data comprising one or more PWV measurements at the first target pressure level;
   while the pressure applied to the portion of the user is at a second target pressure level at a second time, obtaining one or more second sensor measurements from the blood vessel of the user, the one or more second sensor measurements correlating to second data of the characteristic of the blood vessel, the second data comprising one or more PWV measurements at the second target pressure level; and
   determine a physiological parameter of the user by implementing a predictive model based at least on the first data and the second data of the characteristic of the blood vessel, wherein the physiological parameter comprises blood pressure.

\* \* \* \* \*